(12) United States Patent
Kawamura

(10) Patent No.: US 11,918,402 B2
(45) Date of Patent: Mar. 5, 2024

(54) RADIATION IMAGE PROCESSING DEVICE, RADIATION IMAGE PROCESSING METHOD, AND RADIATION IMAGE PROCESSING PROGRAM

(71) Applicant: FUJIFILM Corporation, Tokyo (JP)

(72) Inventor: Takahiro Kawamura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 47 days.

(21) Appl. No.: 17/731,457

(22) Filed: Apr. 28, 2022

(65) Prior Publication Data

US 2022/0249049 A1 Aug. 11, 2022

Related U.S. Application Data

(63) Continuation of application No. PCT/JP2020/040149, filed on Oct. 26, 2020.

(30) Foreign Application Priority Data

Nov. 20, 2019 (JP) ................................. 2019-210027

(51) Int. Cl.
*A61B 6/00* (2006.01)

(52) U.S. Cl.
CPC .......... *A61B 6/5282* (2013.01); *A61B 6/4291* (2013.01); *A61B 6/505* (2013.01)

(58) Field of Classification Search
CPC ....... A61B 6/52; A61B 6/5205; A61B 6/5211; A61B 6/5258; A61B 6/5282; A61B 6/544; A61B 6/545; A61B 6/58
See application file for complete search history.

(56) References Cited

U.S. PATENT DOCUMENTS

2011/0305405 A1 12/2011 Kawamura
2015/0342554 A1 12/2015 Mentrup et al.
(Continued)

FOREIGN PATENT DOCUMENTS

JP 2000-139901 A 5/2000
JP 2011-255060 A 12/2011
(Continued)

OTHER PUBLICATIONS

The extended European search report issued by the European Patent Office dated Nov. 17, 2022, which corresponds to European Patent Application No. 20891205.5-1126 and is related to U.S. Appl. No. 17/731,457.
(Continued)

*Primary Examiner* — Carolyn A Pehlke
(74) *Attorney, Agent, or Firm* — Studebaker & Brackett PC

(57) ABSTRACT

An imaging condition acquisition unit acquires an imaging condition in a case in which a subject is imaged in a state in which an object is interposed between the subject and a radiation detector. A body thickness derivation unit derives a body thickness distribution of the subject based on the radiation image and the imaging condition. A characteristic acquisition unit acquires a radiation characteristic of the object in accordance with the body thickness distribution. A ray distribution unit derives a primary ray distribution and a scattered ray distribution of the radiation detected by the radiation detector by using the imaging condition, the body thickness distribution, and the radiation characteristic. A calculation unit updates the body thickness distribution such that an error between a sum of the primary ray distribution and the scattered ray distribution and a pixel value at each position of the radiation image is smaller than a predetermined threshold value, and repeats the derivation of the (Continued)

radiation characteristic based on the updated body thickness distribution and the derivation of the primary ray distribution and the scattered ray distribution.

10 Claims, 20 Drawing Sheets

(56) References Cited

U.S. PATENT DOCUMENTS

| | | |
|---|---|---|
| 2016/0089094 A1 | 3/2016 | Kawamura et al. |
| 2016/0093030 A1 | 3/2016 | Naito et al. |
| 2016/0140720 A1 | 5/2016 | Naito |
| 2016/0354051 A1* | 12/2016 | Enomoto ............. A61B 6/4241 |
| 2017/0116717 A1 | 4/2017 | Naito et al. |
| 2017/0360391 A1 | 12/2017 | Kawamura |
| 2018/0028141 A1* | 2/2018 | Kuwabara ................ A61B 6/56 |
| 2018/0122094 A1 | 5/2018 | Naito |
| 2022/0079543 A1 | 3/2022 | Takahashi |

FOREIGN PATENT DOCUMENTS

| | | |
|---|---|---|
| JP | 2015-043959 A | 3/2015 |
| JP | 2015-223492 A | 12/2015 |
| JP | 2016-067587 A | 5/2016 |
| JP | 2017-225525 A | 12/2017 |
| WO | 2020/241664 A1 | 12/2020 |

OTHER PUBLICATIONS

An Office Action; "Notice of Reasons for Refusal," mailed by the Japanese Patent Office dated Nov. 15, 2022, which corresponds to Japanese Patent Application No. 2021-558241 and is related to U.S. Appl. No. 17/731,457; with English language translation.

International Search Report issued in PCT/JP2020/040149; dated Jan. 12, 2021.

Written Opinion of the International Searching Authority issued in PCT/JP2020/040149; dated Jan. 12, 2021.

* cited by examiner

RADIATION IMAGE PROCESSING DEVICE, RADIATION IMAGE PROCESSING METHOD, AND RADIATION IMAGE PROCESSING PROGRAM

CROSS REFERENCE TO RELATED APPLICATIONS

The present application is a Continuation of PCT International Application No. PCT/JP2020/040149, filed on Oct. 26, 2020, which claims priority to Japanese Patent Application No. 2019-210027, filed on Nov. 20, 2019. Each application above is hereby expressly incorporated by reference, in its entirety, into the present application.

BACKGROUND

Technical Field

The present disclosure relates to a radiation image processing device, a radiation image processing device, a radiation image processing method, and a radiation image processing program that remove a scattered ray component included in a radiation image.

Related Art

In the related art, in a case in which a radiation image of a subject is captured with radiation transmitted through the subject, particularly in a case in which the thickness of the subject is large, there is a problem that the radiation is scattered in the subject to generate scattered rays, and the contrast of the acquired radiation image is lowered by the scattered rays. Therefore, when the radiation image is captured, the imaging may be performed by disposing a scattered ray removal grid (hereinafter, simply referred to as grid) between the subject and a radiation detector such that the radiation detector that detects the radiation to acquire the radiation image is not irradiated with scattered rays. In a case in which the imaging is performed by using the grid, since the radiation detector is difficult to be irradiated with the radiation scattered by the subject, the contrast of the radiation image can be improved.

The radiation image is captured without using the grid, and an image quality improvement effect obtained by removing the scattered rays using the grid is given to the radiation image by image processing (see JP2015-043959A). A method disclosed in JP2015-043959A is a method of estimating a body thickness distribution of a subject and estimating a scattered ray component by using the estimated body thickness distribution to perform scattered ray removal processing. In addition, a method is also proposed in which, in a case in which the scattered ray removal signal for removing the scattered rays is calculated, the radiation image is made to be close to the image quality in a case in which the grid is actually used by calibrating, in advance, the radiation selectivity and the contrast improvement in a case in which the grid is used by imaging the actual grid (JP2015-223492A).

In addition, a method is also proposed in which, in order to remove a scattered ray component from a radiation image in consideration of an air gap between a subject and a radiation detector, an imaging condition when the radiation image is acquired, distance information representing a distance including the air gap between the subject and the radiation detector is acquired, scattered ray component information representing the scattered ray component of the radiation included in the radiation image is acquired based on the imaging condition, a ratio of scattered ray dose that reaches the radiation detector in accordance with an estimated body thickness distribution of the subject and the distance information is acquired, the scattered ray component information is corrected based on the acquired ratio, and scattered ray removal processing of the radiation image is performed based on the corrected scattered ray component information (JP2017-225525A).

By the way, in a case in which the radiation imaging of the subject is actually performed, the grid may be used between the subject and the radiation detector, or an object, such as an imaging table or a top plate of the imaging table, may be interposed. Since such an object has a unique radiation characteristic, the radiation qualities of a primary ray component and the scattered ray component are changed in accordance with the radiation characteristic of the object by being transmitted through the object. Therefore, a body thickness of the subject cannot be estimated with high accuracy or the scattered ray component cannot be removed with high accuracy unless the radiation characteristic of the object interposed between the subject and the radiation detector are taken into consideration.

SUMMARY OF THE INVENTION

The present invention has been made in view of the above circumstances, and is to acquire the radiation image from which the scattered ray component is removed with high accuracy in consideration of the object interposed between the subject and the radiation detector.

The present disclosure relates to a radiation image processing device comprising at least one processor, in which the processor is configured to acquire an imaging condition in a case in which a radiation image of a subject is acquired by a radiation detector detecting radiation transmitted through the subject in a state in which an object is interposed between the subject and the radiation detector, derive a body thickness distribution of the subject based on the radiation image and the imaging condition, acquire a radiation characteristic of the object in accordance with the body thickness distribution, derive a primary ray distribution and a scattered ray distribution of the radiation detected by the radiation detector by using the imaging condition, the body thickness distribution, and the radiation characteristic of the object, and derive an error between a sum of the primary ray distribution and the scattered ray distribution and a pixel value at each position of the radiation image, update the body thickness distribution such that the error is smaller than a predetermined threshold value, and repeat derivation of the radiation characteristic based on the updated body thickness distribution and derivation of the primary ray distribution and the scattered ray distribution.

Note that, in the radiation image processing device according to the present disclosure, the processor may be configured to output a processed radiation image including, as a pixel value, the primary ray distribution derived based on the body thickness distribution of the subject in which the error is smaller than the threshold value.

In addition, the radiation image processing device according to the present disclosure may further comprise a storage unit that stores the radiation characteristic measured in advance by using an imaging system that acquires the radiation image, in which the processor is configured to acquire the radiation characteristic stored in the storage unit.

In addition, the radiation image processing device according to the present disclosure, the object may be at least one of an imaging table on which the subject is placed, a top plate, a scattered ray removal grid, or an air layer.

In addition, the radiation image processing device according to the present disclosure, the radiation characteristic may be a primary ray transmittance and a scattered ray transmittance.

In addition, the radiation image processing device according to the present disclosure, the processor may be configured to acquire a processed radiation image for each of two radiation images based on radiation having different energy distributions and transmitted through the subject, and derive a subtraction image obtained by extracting a specific structure of the subject by performing weighting subtraction between corresponding pixels of two processed radiation images.

In addition, the radiation image processing device according to the present disclosure, the processor may be configured to acquire a processed radiation image for each of two radiation images based on radiation having different energy distributions and transmitted through a subject including a bone part and a soft part, derive a bone part image obtained by extracting the bone part of the subject by performing weighting subtraction between corresponding pixels of two processed radiation images, and derive bone mineral information representing a bone mineral density in a bone region in the bone part image for each pixel of the bone region based on the imaging condition, the body thickness distribution, and a pixel value of the bone region.

In addition, the radiation image processing device according to the present disclosure, the processor may be configured to irradiate the subject with the radiation from a plurality of projection angles to acquire a processed radiation image for each of a plurality of radiation images corresponding to each of the plurality of projection angles, and reconstruct a plurality of the processed radiation images to generate a tomographic image of the subject.

The present disclosure relates to a radiation image processing method comprising acquiring an imaging condition in a case in which a radiation image of a subject is acquired by a radiation detector detecting radiation transmitted through the subject in a state in which an object is interposed between the subject and the radiation detector, deriving a body thickness distribution of the subject based on the radiation image and the imaging condition, acquiring a radiation characteristic of the object in accordance with the body thickness distribution, deriving a primary ray distribution and a scattered ray distribution of the radiation detected by the radiation detector by using the imaging condition, the body thickness distribution, and the radiation characteristic of the object, and deriving an error between a sum of the primary ray distribution and the scattered ray distribution and a pixel value at each position of the radiation image, updating the body thickness distribution such that the error is smaller than a predetermined threshold value, and repeating derivation of the radiation characteristic based on the updated body thickness distribution and derivation of the primary ray distribution and the scattered ray distribution.

Note that the radiation image processing method according to the present disclosure may be provided as a radiation image processing program to be executed by a computer.

According to the present disclosure, it is possible to acquire the radiation image from which the scattered ray component is removed with high accuracy in consideration of the object interposed between the subject and the radiation detector.

DETAILED DESCRIPTION

Figure 1:
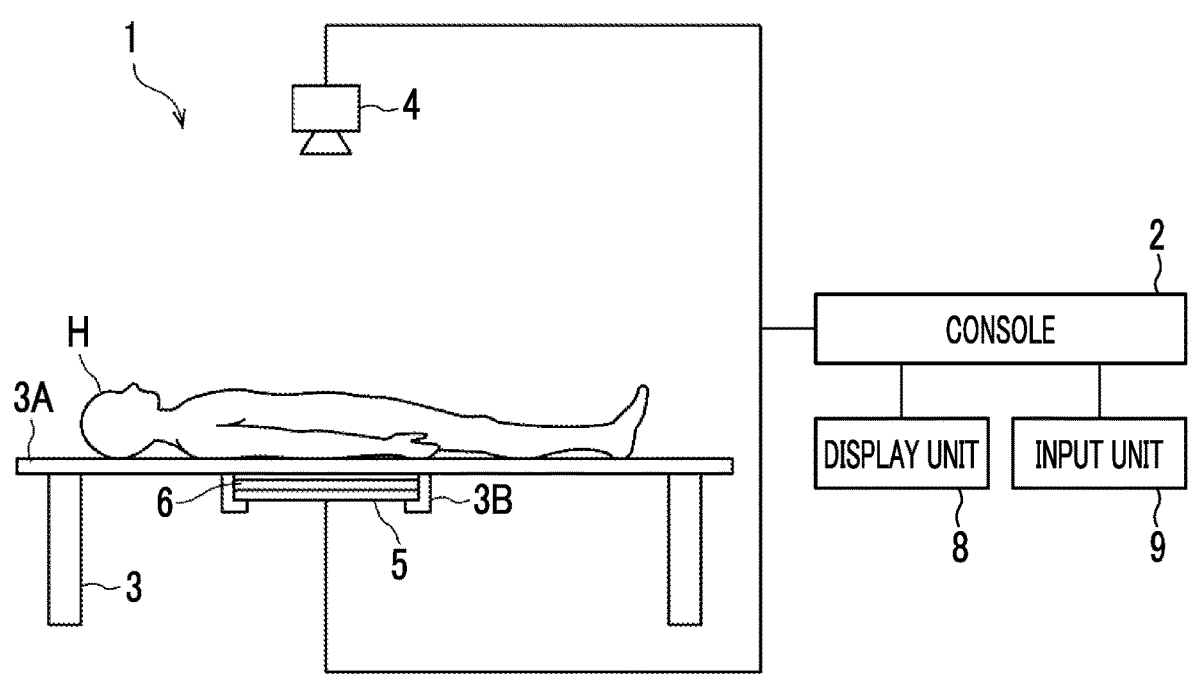
FIG. 1 is a schematic block diagram showing a configuration of a radiography system to which a radiation image processing device according to a first embodiment of the present disclosure is applied.

In the following, embodiments of the present disclosure will be described with reference to the drawings. FIG. 1 is a schematic block diagram showing a configuration of a radiography system to which a radiation image processing device according to a first embodiment of the present disclosure is applied. As shown in FIG. 1, the radiography system according to the first embodiment is a system that images a subject by using a scattered ray removal grid and removes a scattered ray component of radiation transmitted through the subject, which is included in the radiation image acquired by imaging the subject, and comprises an imaging apparatus 1 and a console 2 that encompasses a radiation image processing device according to the present embodiment.

The imaging apparatus 1 is an imaging apparatus that acquires a radiation image G0 of a subject H lying down on an imaging table 3 by irradiating a radiation detector 5 with the radiation emitted from a radiation source 4, such as an X-ray source, and transmitted through the subject H. Note that the radiation source 4 is provided with a collimator (irradiation field stop) (not shown). As a result, a range of the radiation emitted to the subject H is defined. The radiation image G0 is input to the console 2, which is the radiation image processing device. Here, in the present embodiment, a scattered ray removal grid (hereinafter, simply referred to as a grid) 6 for removing the scattered ray component scattered by the subject H in the radiation transmitted through the subject H is disposed between a top plate 3A of the imaging table 3 and the radiation detector 5.

The grid 6 is configured by lead that does not transmit the radiation and an interspace material, such as aluminum or fiber that easily transmit the radiation which are disposed alternately with a fine grid density of about 4.0 lines/mm.

By using the grid 6, a scattered ray component of the radiation transmitted through the subject H can be removed, but it cannot be completely removed. Therefore, the radiation image G0 acquired by the radiation detector 5 includes the scattered ray component as well as a primary ray component of the radiation transmitted through the subject H.

The radiation detector 5 can repeatedly perform recording and reading-out of the radiation image, and a so-called direct type radiation detector that directly receives irradiation of the radiation to generate a charge may be used. In addition, a so-called indirect type radiation detector that once converts the radiation into visible light and then converts the visible light into a charge signal may be used. In addition, as a method for reading out a radiation image signal, it is desirable to use a so-called thin film transistor (TFT) readout method in which the radiation image signal is read out by turning a TFT switch on and off, or a so-called optical readout method in which the radiation image signal is read out by emission of read out light. However, other methods may also be used without being limited to these methods.

In addition, the radiation detector 5 is a portable radiation detector, and is detachably attached to the imaging table 3 together with the grid 6 by an attachment portion 3B provided on a lower surface of the top plate 3A of the imaging table 3. Note that the radiation detector 5 may be fixed to the imaging table 3.

A display unit 8 and an input unit 9 are connected to the console 2. The display unit 8 includes a cathode ray tube (CRT), a liquid crystal display, or the like, and displays the radiation image acquired by imaging or assists various inputs necessary for the processing performed in the console 2.

The input unit 9 includes a keyboard, a mouse, or an input device of a touch panel type, and receives an instruction for operating the imaging apparatus 1 from an operator. In addition, the input unit 9 also receives inputs of various pieces of information necessary for the imaging, such as an imaging condition, and an instruction for correcting information. In the present embodiment, each unit of the imaging apparatus 1 is operated according to the information input by the operator from the input unit 9.

A radiation image processing program according to the first embodiment is installed in the console 2. The console 2 corresponds to the radiation image processing device according to the first embodiment. In the first embodiment, the console 2 may be a workstation or a personal computer which is directly operated by the operator, or may be a server computer which is connected to the workstation or the personal computer via a network. The radiation image processing program is stored in a storage device of the server computer connected to the network or in a network storage to be accessible from the outside, and is downloaded and installed in the computer as necessary. Alternatively, the radiation image processing program is distributed by being recorded on a recording medium, such as a digital versatile disc (DVD) or a compact disc read only memory (CD-ROM), and is installed in the computer from the recording medium.

Figure 2:
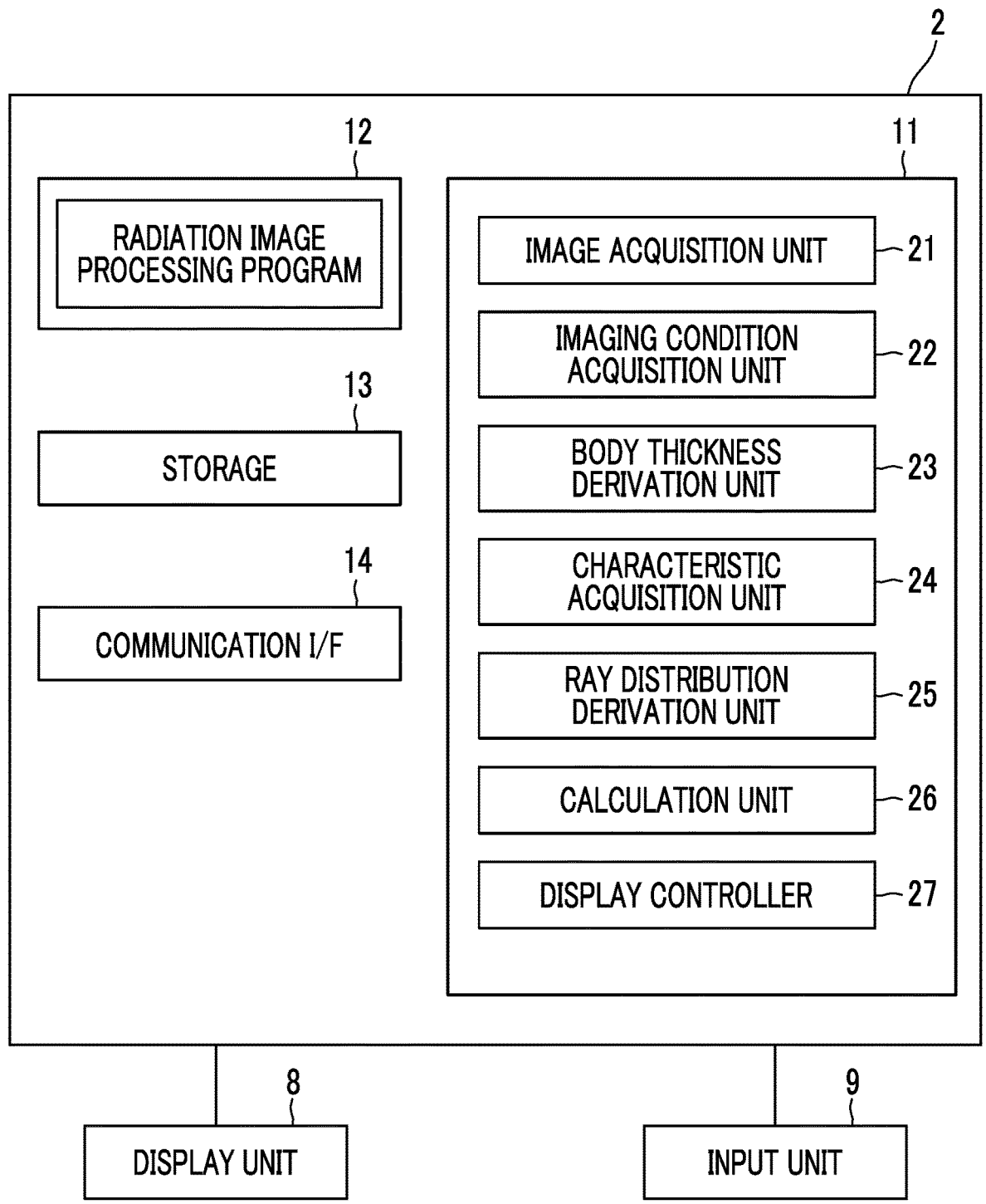
FIG. 2 is a diagram showing a schematic configuration of the radiation image processing device according to the first embodiment.

FIG. 2 is a diagram showing a schematic configuration of the radiation image processing device according to the first embodiment, which is realized by installing the radiation image processing program according to the first embodiment on the computer configuring the console 2. As shown in FIG. 2, the radiation image processing device according to the first embodiment comprises a central processing unit (CPU) 11, a memory 12, a storage 13, and a communication interface (I/F) 14 as a standard computer configuration.

The storage 13 is a storage device, such as a hard disk drive or a solid state drive (SSD), and stores various pieces of information including a program for driving each unit of the imaging apparatus 1 and the radiation image processing program. In addition, the radiation image acquired by imaging is stored in the storage 13.

The communication I/F 14 is a network interface that performs a transmission control of various pieces of information between an external apparatus and the console 2 via the network (not shown).

The memory 12 transitorily stores the program and the like stored in the storage 13 in order to cause the CPU 11 to execute various processing. The radiation image processing program defines, as the processing to be executed by the CPU 11, image acquisition processing of causing the imaging apparatus 1 to perform imaging to acquire the radiation image G0, imaging condition acquisition processing of acquiring the imaging condition in a case where the subject H is imaged, body thickness derivation processing of deriving the body thickness distribution of the subject H based on the radiation image G0 and the imaging condition, characteristic acquisition processing of acquiring the radiation characteristic of the object interposed between the subject H of the imaging apparatus 1 and the radiation detector 5 in accordance with the body thickness distribution, ray distribution derivation processing of deriving the primary ray distribution and the scattered ray distribution of the radiation detected by the radiation detector 5 by using the imaging condition, the body thickness distribution, and the radiation characteristic of the object, and calculation processing of deriving an error between a sum of the primary ray distribution and the scattered ray distribution and a pixel value at each position of the radiation image, updating the body thickness distribution such that the error is smaller than a predetermined threshold value, repeating derivation of the radiation characteristic based on the updated body thickness distribution, and derivation of the primary ray distribution and the scattered ray distribution, and output a processed radiation image Gm including, as the pixel value, the primary ray distribution derived based on the body thickness distribution of the subject H in which the error is smaller than the predetermined threshold value, and display control processing of displaying the processed radiation image Gm on the display unit 8.

Moreover, by the CPU 11 executing these processing according to the radiation image processing program, the console 2 functions as an image acquisition unit 21, an imaging condition acquisition unit 22, a body thickness derivation unit 23, a characteristic acquisition unit 24, a ray distribution derivation unit 25, a calculation unit 26, and a display controller 27.

The image acquisition unit 21 drives the radiation source 4 to irradiate the subject H with the radiation and detects the radiation transmitted through the subject H by using the radiation detector 5 to acquire the radiation image G0 of the subject H. In the present embodiment, the top plate 3A of the imaging table 3 and the grid 6 are interposed between the subject H and the radiation detector 5. In this case, the radiation transmitted through the subject H is transmitted through the top plate 3A and the grid 6 and emitted to the radiation detector 5.

Note that, in a case in which the subject H is imaged, imaging conditions are set. As the imaging conditions, the radiation quality of the radiation, dose, and imaging distance at the time of imaging (source-to-image receptor distance (SID)) are used. The radiation quality is defined by using one or more of the tube voltage [kV] of a radiation generator in the radiation source 4, a total filtration amount [mmAl equivalent], or a half-value layer [mmAl]. The tube voltage means the maximum value of the generated radiation energy distribution. The total filtration amount is obtained by converting the filtration amount of each constituting component which configures the imaging apparatus 1, such as a radiation generator and a collimator, in the radiation source 4 into a thickness of the aluminum. The influence of the beam hardening in the imaging apparatus 1 is larger and the total amount of high-energy components in the wavelength distribution of the radiation is larger as the total filtration amount is larger. The half-value layer is defined by the thickness of the aluminum necessary to attenuate the dose in half with respect to the generated radiation energy distribution. The high-energy components in the wavelength distribution of the radiation is larger as the aluminum in the half-value layer is thicker.

The dose is defined by using any of the tube current time product [mAs] or the irradiation dose [mR] of the radiation generator at the radiation source 4. In addition, the SID is a distance [cm] between the radiation source 4 and the detector of the radiation detector 5.

Note that, when the subject H is imaged, the imaging conditions are determined according to the imaging technique. Therefore, in the present embodiment, a table in which various imaging techniques and the imaging conditions are associated with each other is stored in the storage 13 in advance. At the time of imaging, in a case in which the operator designates the imaging technique from the input unit 9, the table stored in the storage 13 is referred to, the imaging conditions corresponding to the imaging techniques are read out from the table, and imaging of the subject H is performed according to the read out imaging conditions. The imaging conditions used at the time of imaging are transitorily stored in the memory 12 or the storage 13. Note that the imaging conditions are not limited to the imaging conditions corresponding to the imaging techniques, and may be designated by the input of the operator using the input unit 9.

The imaging condition acquisition unit 22 acquires the imaging conditions used when the subject H is imaged by reading out the imaging conditions from the memory 12 or the storage 13.

The body thickness derivation unit 23 derives the body thickness distribution of the subject H based on the radiation image G0 and the imaging conditions. In the following, the body thickness distribution derived by the body thickness derivation unit 23 is referred to as an initial body thickness distribution t0. In the following, the derivation of the initial body thickness distribution t0 will be described.

First, in a case in which the radiation source 4 is driven to emit the radiation to the radiation detector 5 in a state in which the subject H is not present, a reaching dose $I0(x,y)$ of the radiation emitted from the radiation source 4 to the radiation detector 5 is represented by Expression (1). In Expression (1), mAs included in the imaging conditions is a tube current-time product, and kV is the tube voltage. Note that the half-value layer is also taken into consideration, the reaching dose $I0(x,y)$ is represented by Expression (1-1). Here, F is a non-linear function that represents the radiation dose that reaches to the radiation detector 5 in a case in which the dose (for example, 1 mAs), which is a standard, is emitted to the radiation detector 5 at the SID (for example, 100 cm), which is a standard, in a state in which the subject H is not present. F is changed for each tube voltage or depending on the tube voltage and the half-value layer. In addition, since the reaching dose I0 is derived for each pixel of the radiation image G0 acquired by the radiation detector 5, (x,y) represents the pixel position of each pixel. In addition, in the following description, in order to include both a case in which the half-value layer is considered and a case in which the half-value layer is not considered, each expression is represented by including mmAl in parentheses as shown in Expression (1-2).

$$I0(x,y)=\text{mAs}\times F(\text{kV})/\text{SID}^2 \quad (1)$$

$$I0(x,y)=\text{mAs}\times F(\text{kV},\text{mmAl})/\text{SID}^2 \quad (1\text{-}1)$$

$$I0(x,y)=\text{mAs}\times F(\text{kV},(\text{mmAl}))/\text{SID}^2 \quad (1\text{-}2)$$

In addition, in a case in which the initial body thickness distribution is defined as t0, the attenuation coefficient of the subject H in a case of having the initial body thickness distribution t0 is defined as $\mu(t0)$, and a scatter-to-primary ratio, which is a ratio between the scattered ray dose and a primary ray dose included in the radiation after being transmitted through the subject H having the initial body thickness distribution t0 in a case in which a scattered ray spread is not considered is defined as STPR(t0), the dose I1 after being transmitted through the subject H is represented by Expression (2). Note that, in Expression (2), the initial body thickness distribution t1, the reaching dose I0, and the dose I1 are derived for each pixel of the radiation image G0, but (x,y) is omitted. In addition, STPR is a non-linear function that depends on the tube voltage [kV] and the half-value layer [mmAl] in addition to the body thickness, but in Expression (2), kV and mmAl are omitted.

$$I1=I0\times\exp\{-\mu(t0)\times t0\}\times\{1+\text{STPR}(t0)\} \quad (2)$$

In Expression (2), the dose I1 is a pixel value in each pixel of the radiation image G0, and the reaching dose I0 is derived by Expressions (1) and (1-1). On the other hand, since F and STPR are non-linear functions, Expression (2) cannot be algebraically solved for t0 Therefore, the body thickness derivation unit 23 defines an error function E11 shown in Expression (3) or Expression (3-1). Moreover, t0 at which the error function E1 is minimized or the error function E1 is smaller than a predetermined threshold value Th1 is derived as the initial body thickness distribution. In this case, the body thickness derivation unit 23 derives the initial body thickness distribution t0 by using an optimization algorithm, such as the steepest descent method and the conjugate gradient method.

$$E1 = [I1 - I0 \times \exp\{-\mu(t0) \times t0\} \times \{1 + STPR(t0)\}]^2 \quad (3)$$

$$E1 = [I1 - I0 \times \exp\{-\mu(t0) \times t0\} \times \{1 + STPR(t0)\}] \quad (3)$$

The characteristic acquisition unit 24 acquires the radiation characteristic of the object interposed between the subject H and the radiation detector 5 at the time of imaging Here, in a case in which the radiation after being transmitted through the subject H is transmitted through the object interposed between the subject H and the radiation detector 5, a transmittance of the radiation is changed depending on the radiation quality of the radiation after being transmitted through the subject H. In addition, a primary ray transmittance and a scattered ray transmittance included in the radiation after being transmitted through the subject H are different due to the difference in the traveling direction of the radiation and the radiation quality. Therefore, in the present embodiment, as the radiation characteristic of the object, the primary ray transmittance and the scattered ray transmittance of the object are used.

Note that, as described above, in a case in which the radiation after being transmitted through the subject H is transmitted through the object interposed between the subject H and the radiation detector 5, a transmittance of the radiation is changed depending on the radiation quality of the radiation after being transmitted through the subject H. In addition, the radiation quality of the radiation after being transmitted through the subject H depends on the body thickness distribution t of the subject H. Therefore, the primary ray transmittance and the scattered ray transmittance can be represented by Tp(t) and Ts(t), respectively, as functions of the body thickness t of the subject H.

Note that the radiation quality of the radiation after being transmitted through the subject H also depends on the radiation quality of the radiation source 4 included in the imaging conditions. The radiation quality depends on the tube voltage and the half-value layer. Therefore, strictly speaking, the primary ray transmittance and the scattered ray transmittance are represented by Tp(kV(, mmAl), t) and Ts(kV(, mmAl), t), respectively. Note that, in the following description, the primary ray transmittance and the scattered ray transmittance may be simply represented by Tp and Ts.

Here, as described above, a primary ray transmittance Tp and a scattered ray transmittance Ts of the object interposed between the subject H and the radiation detector 5 depend on the body thickness distribution t of the subject H. Therefore, in the present embodiment, the primary ray transmittance Tp and the scattered ray transmittance Ts of the object in accordance with the body thickness distribution t of the subject H are measured by using phantom with various thicknesses that imitate the body thickness distribution t of the subject, a table that defines a relationship between the body thickness distribution t of the subject H and the primary ray transmittance Tp and the scattered ray transmittance Ts of the object is generated based on a result of measurement and stored in the storage 13. In the following, the measurement of the primary ray transmittance Tp and the scattered ray transmittance Ts of the object in accordance with the body thickness distribution t of the subject H will be described.

Figure 3:
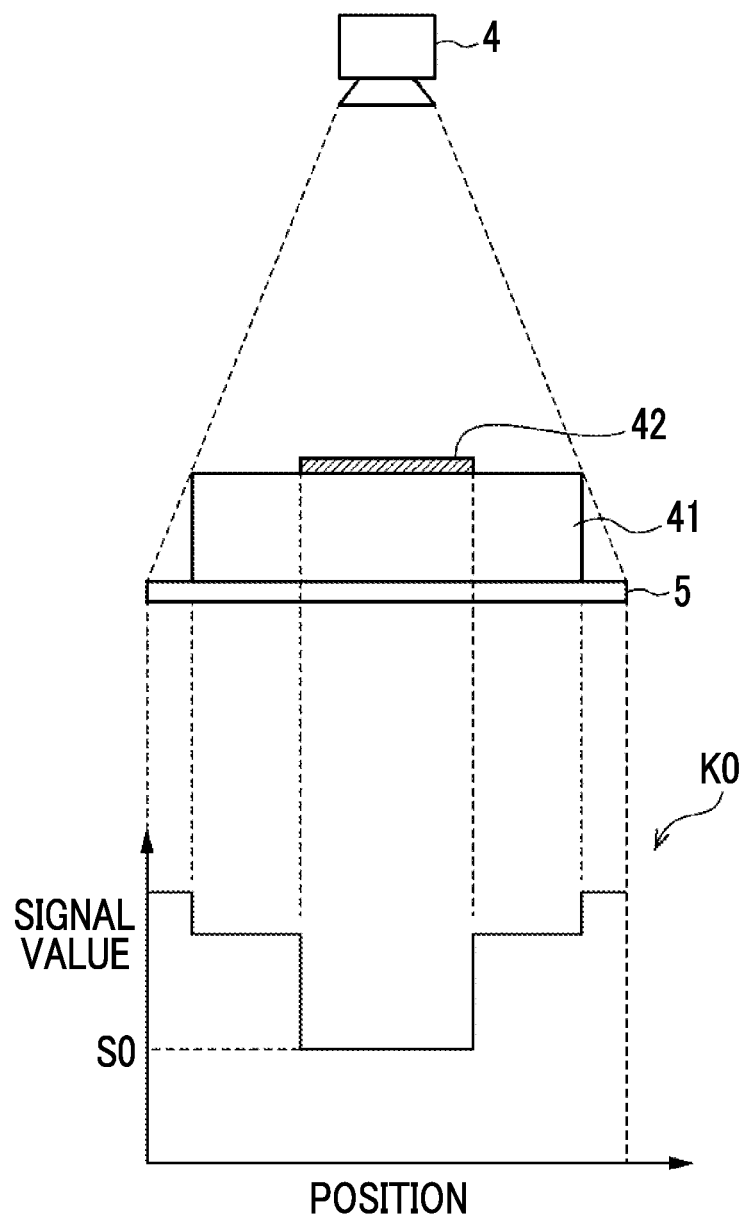
FIG. 3 is a diagram for describing measurement of a scattered ray transmittance in accordance with a body thickness of a subject.
Figure 4:
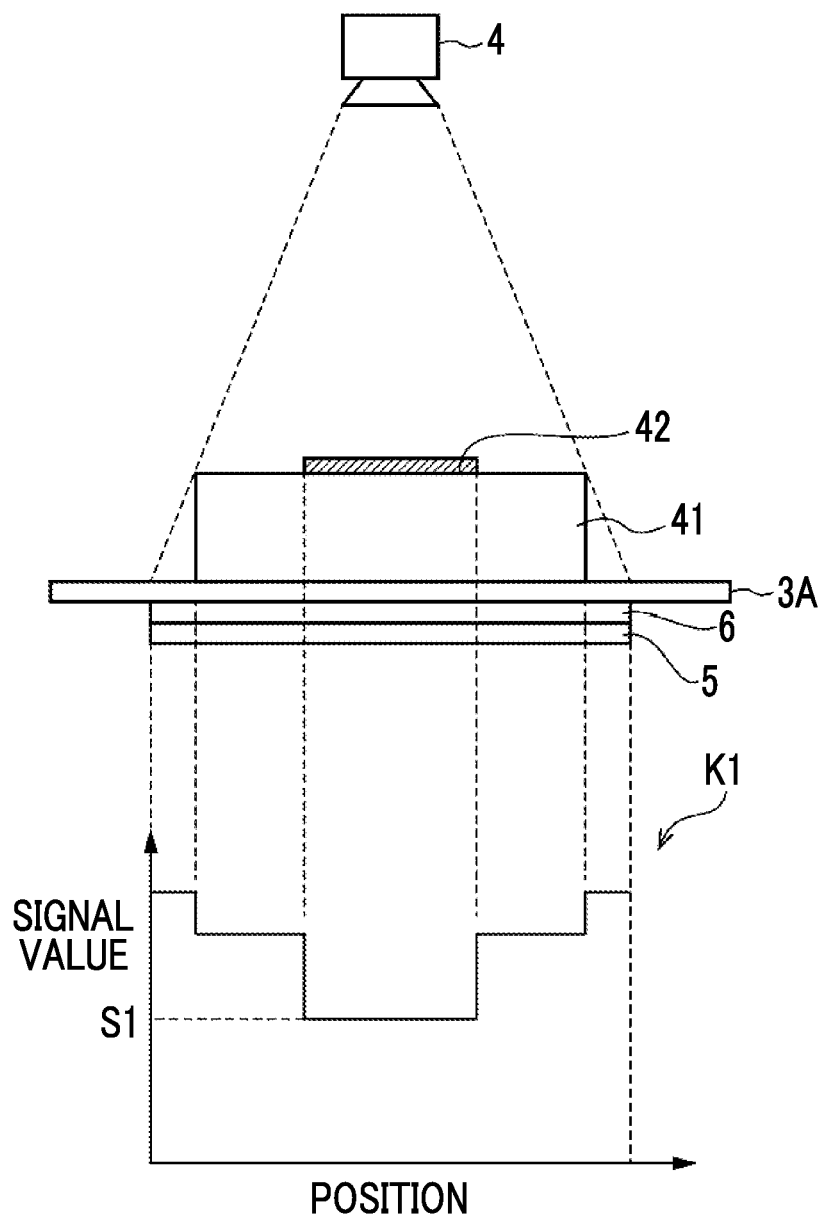
FIG. 4 is a diagram for describing the measurement of the scattered ray transmittance in accordance with the body thickness of the subject.

First, the calculation of the scattered ray transmittance Ts will be described. FIGS. 3 and 4 are diagrams for describing the measurement of the scattered ray transmittance Ts in accordance with the body thickness of the subject H. First, as shown in FIG. 3, a phantom 41 that imitates the human body is placed on a surface of the radiation detector 5, and a lead plate 42 is further placed on the phantom 41. Here, the phantom 41 has various thicknesses, such as 5 cm, 10 cm, and 20 cm, and is made of a material, such as acrylic, having a radiation transmittance similar to that of water, for example. In this state, by driving the radiation source 4 and irradiating the radiation detector 5 with the radiation, the characteristic acquisition unit 24 acquires a radiation image K0 for measurement. A signal value of the radiation image K0 is larger in the region in which the radiation is directly emitted to the radiation detector 5, and the signal value is smaller in the order of the region of the phantom 41 and the region of the lead plate 42.

Note that, since the lead plate 42 does not transmit the radiation, the signal value should be 0 in a region of the lead plate 42 in the radiation image K0. However, the radiation scattered by the phantom 41 reaches a region corresponding to the lead plate 42 of the radiation detector 5. Therefore, the region of the lead plate 42 in the radiation image K0 has a signal value S0 corresponding to the scattered ray component by the phantom 41.

Then, as shown in FIG. 4, the phantom 41 is placed on the top plate 3A of the imaging apparatus 1, and the lead plate 42 is further placed on the phantom 41. Moreover, as in a case of imaging the subject H, the characteristic acquisition unit 24 acquires a radiation image K1 for measurement by driving the radiation source 4 to irradiate the radiation detector 5 with the radiation in a state in which the radiation detector 5 and the grid 6 are disposed below the top plate 3A. Similar to the radiation image K0, a signal value of the radiation image K1 is larger in the region in which the radiation is directly emitted to the radiation detector 5, and the signal value is smaller in the order of the region of the phantom 41 and the region of the lead plate 42. Here, as shown in FIG. 4, in a case in which imaging is performed in a state in which the top plate 3A and the grid 6 are interposed between the phantom 41 and the radiation detector 5, the radiation scattered by the top plate 3A and the grid 6 also reaches the region corresponding to the lead plate 42 of the radiation detector 5 in addition to the radiation scattered by the phantom 41. Therefore, the region of the lead plate 42 in the radiation image K1 has a signal value S1 corresponding to the scattered ray component by the phantom 41, the top plate 3A, and the grid 6.

Note that, since the signal value S1 includes the scattered ray component due to the top plate 3A and the grid 6, the signal value S1 is larger than the signal value S0 shown in FIG. 3. Therefore, in a case of imaging the phantom 41 having a thickness of t, the scattered ray transmittance Ts of the object interposed between the subject H and the radiation detector 5, that is, the top plate 3A and the grid 6 can be calculated by S1/S0.

Figure 5:
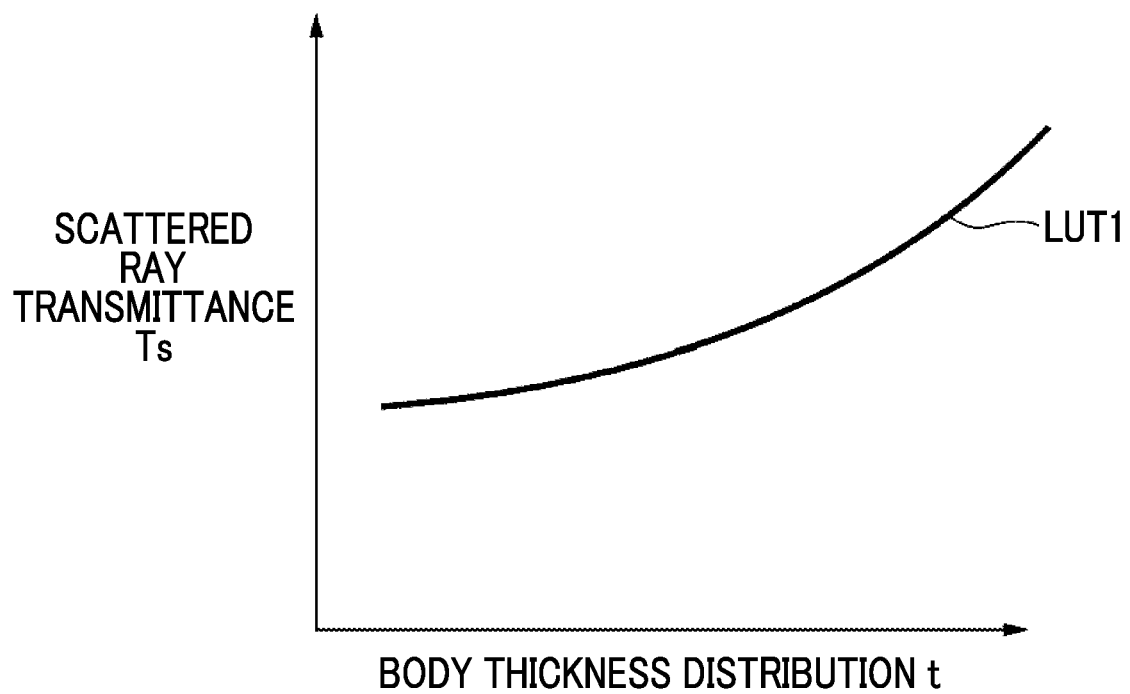
FIG. 5 is a table representing a relationship between a body thickness distribution of the subject and the scattered ray transmittance of an object interposed between the subject and a radiation detector.

In the present embodiment, the characteristic acquisition unit 24 calculates the scattered ray transmittance Ts corresponding to each thickness as shown in FIGS. 3 and 4 by using at least two types of phantoms having different thicknesses. In addition, the characteristic acquisition unit 24 derives the scattered ray transmittance Ts having a thickness that is not present in the phantom 41 by interpolating the scattered ray transmittance Ts for a plurality of measured thicknesses. As a result, as shown in FIG. 5, the characteristic acquisition unit 24 generates a table LUT1 that represents a relationship between the body thickness distribution t of the subject H and the scattered ray transmittance Ts of the object interposed between the subject H and the radiation detector 5 by interpolating the scattered ray transmittance for the thickness between the thicknesses.

Figure 6:
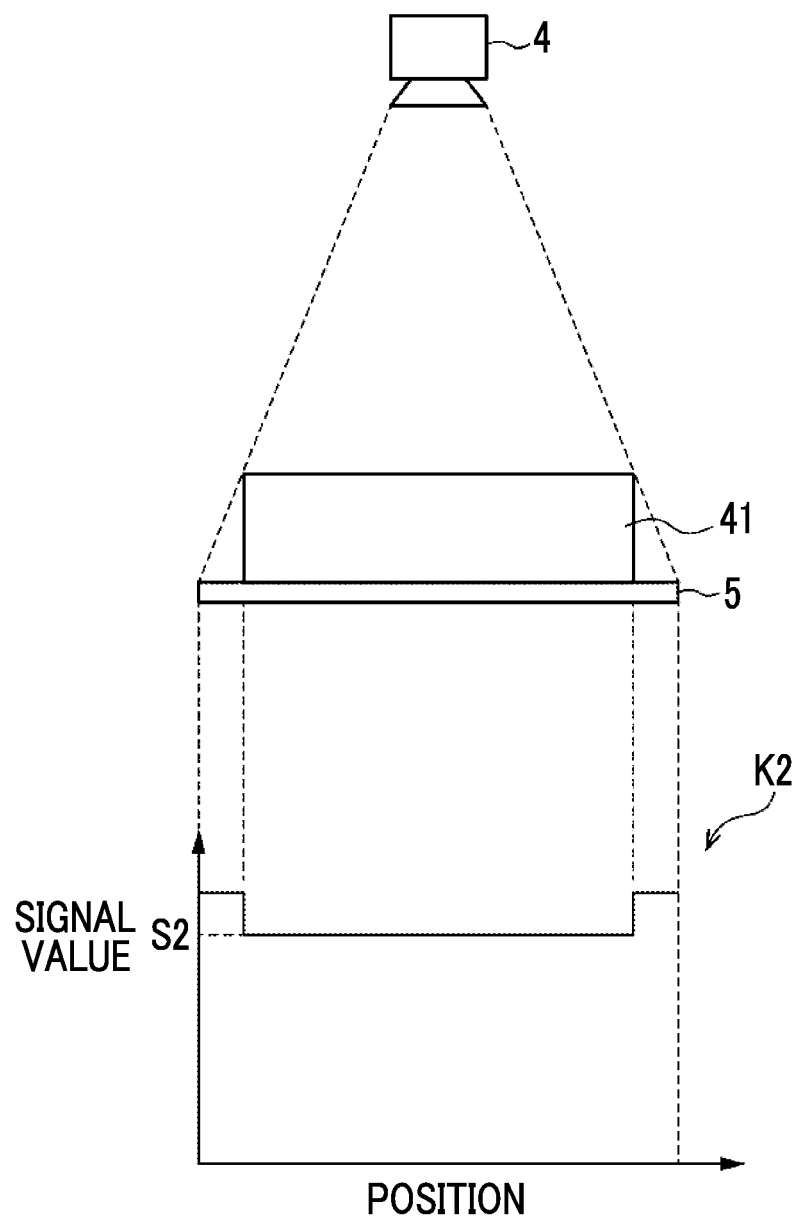
FIG. 6 is a diagram for describing the measurement of a primary ray transmittance in accordance with the body thickness of the subject.
Figure 7:
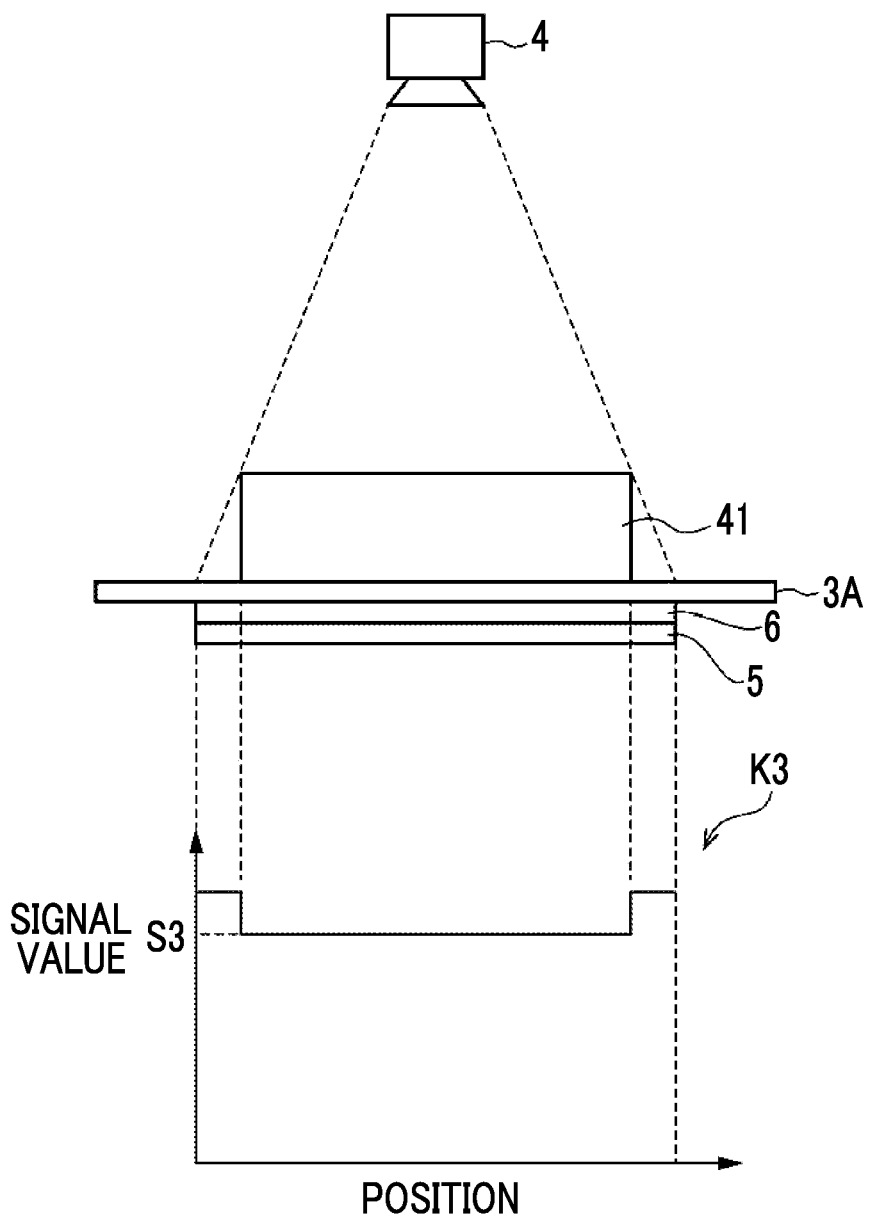
FIG. 7 is a diagram for describing the measurement of the primary ray transmittance in accordance with the body thickness of the subject.

Then, the calculation of the primary ray transmittance will be described. FIGS. 6 and 7 are diagrams for describing the measurement of the primary ray transmittance Tp in accordance with the body thickness of the subject H. First, as shown in FIG. 6, the phantom 41 that imitates the human body is placed on the surface of the radiation detector 5. Here, as the phantom 41, the same phantom as in a case in which the scattered ray transmittance Ts is derived is used. Further, in this state, by driving the radiation source 4 and irradiating the radiation detector 5 with the radiation, the characteristic acquisition unit 24 acquires a radiation image K2 for measurement. A signal value S2 in a region corresponding to the phantom 41 in the radiation image K2 includes both the primary ray component and the scattered ray component of the radiation transmitted through the phantom 41. Here, the scattered ray component of the radiation transmitted through the phantom 41 is the signal value S0 in the radiation image K0 obtained by the method shown in FIG. 3. Therefore, the primary ray component of the radiation transmitted through the phantom 41 is derived by S2-S0.

Then, as shown in FIG. 7, the phantom 41 is placed on the top plate 3A of the imaging apparatus 1, and as in a case of imaging the subject H, the characteristic acquisition unit 24 acquires a radiation image K3 for measurement by driving the radiation source 4 to irradiate the radiation detector 5 with the radiation in a state in which the radiation detector 5 and the grid 6 are disposed below the top plate 3A. A signal value S3 in a region corresponding to the phantom 41 in the radiation image K3 includes both the primary ray component and the scattered ray component of the radiation transmitted through the phantom 41, the top plate 3A, and the grid 6. Here, the scattered ray component of the radiation transmitted through the phantom 41, the top plate 3A, and the grid 6 is the signal value S1 in the radiation image K1 obtained by the method shown in FIG. 4. Therefore, the primary ray component of the radiation transmitted through the phantom 41, the top plate 3A, and the grid 6 is derived by S3-S1.

Figure 8:
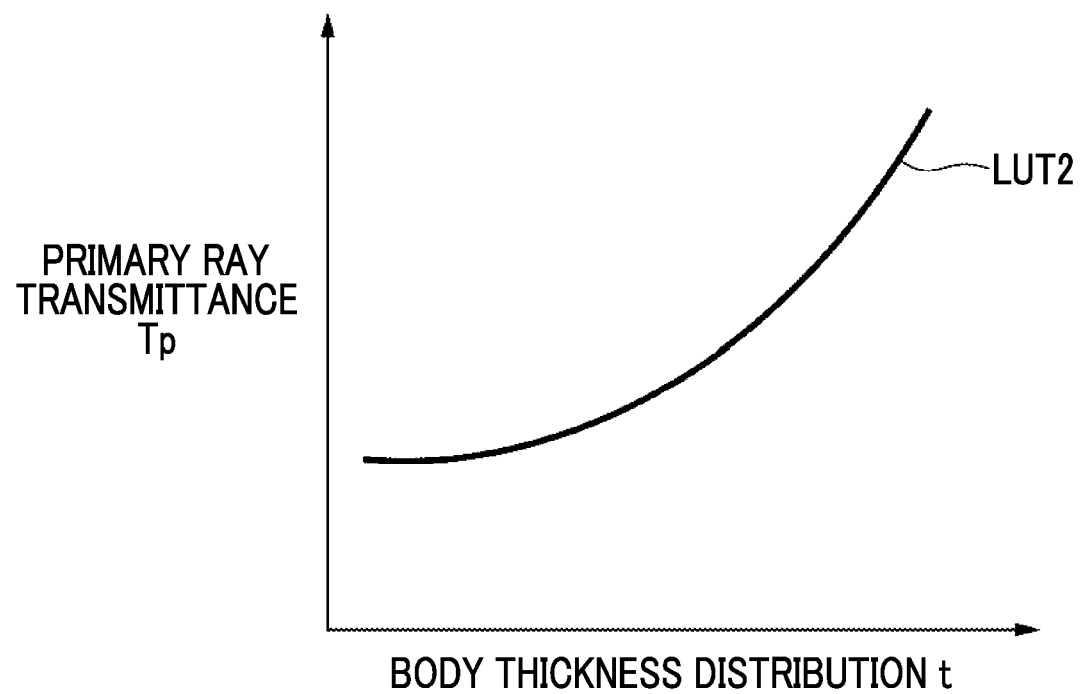
FIG. 8 is a table representing a relationship between the body thickness distribution of the subject and the primary ray transmittance of the object interposed between the subject and the radiation detector.

Therefore, it is possible to calculate, by (S3−S1)/(S0−S2), the primary ray transmittance Tp of the top plate 3A and the grid 6 interposed between the subject H and the radiation detector 5 in a case in which the phantom 41 is imaged. Moreover, in the present embodiment, the characteristic acquisition unit 24 calculates the primary ray transmittance Tp corresponding to each thickness as shown in FIGS. 6 and 7 by using at least two types of phantoms having different thicknesses. In addition, the characteristic acquisition unit 24 derives the primary ray transmittance Tp having a thickness that is not present in the phantom 41 by interpolating the primary ray transmittance Tp for a plurality of measured thicknesses. As a result, as shown in FIG. 8, the characteristic acquisition unit 24 generates a table LUT2 that represents a relationship between the body thickness distribution t of the subject H and the primary ray transmittance Tp of the object interposed between the subject H and the radiation detector 5.

The tables LUT1 and LUT2 generated as described above are stored in the storage 13. Note that the table is generated depending on various imaging conditions (that is, the radiation quality, the dose, and the radiation source distance), and the type of grid 6 to be used, and is stored in the storage 13.

The characteristic acquisition unit 24 acquires the primary ray transmittance Tp(t0) and the scattered ray transmittance Ts(t0) corresponding to the initial body thickness distribution t0 for the object interposed between the subject H and the radiation detector 5 with reference to the tables LUT1 and LUT2 stored in the storage 13 depending on the imaging conditions acquired by the imaging condition acquisition unit 22. Note that, since the primary ray transmittance Tp and the scattered ray transmittance Ts also depend on the radiation quality, the primary ray transmittance Tp and the scattered ray transmittance Ts can be represented by Tp(kV(, mmAl), t0) and Ts(kV(, mmAl), t0), respectively.

The ray distribution derivation unit 25 derives the primary ray distribution and the scattered ray distribution of the radiation detected by the radiation detector 5 by using the imaging conditions, the body thickness distribution, and the radiation characteristic of the object interposed between the subject H and the radiation detector 5. Here, a primary ray distribution Ip0 and a scattered ray distribution Is0 after being transmitted through the subject H are represented by Expressions (4) and (5) in a case in which the body thickness distribution is defined as t. PSF in Expression (5) is a point spread function that represents the distribution of the scattered rays spreading from one pixel, and is defined depending on the radiation quality and the body thickness. In addition, * indicates a convolution operation. The primary ray distribution Ip0 and the scattered ray distribution Is0 are derived for each pixel of the radiation image G0, but (x,y) are omitted in Expressions (4) and (5). In addition, in the first embodiment, derivation of the body thickness distribution, the primary ray distribution Ip0, and the scattered ray distribution Is0 is repeatedly performed as described below, but in a case of the first derivation of the first primary ray distribution Ip0 and the scattered ray distribution Is0, the initial body thickness distribution t0 is used as the body thickness distribution t.

$$Ip0 = I0 \times \exp\{-\mu(t) \times t\} \quad (4)$$

$$Is0 = Ip0 \times STPR(kV(,mmAl),t) * PSF(kV(,mmAl),t) \quad (5)$$

Moreover, the ray distribution derivation unit 25 derives a primary ray distribution Ip1 and a scattered ray distribution Is1 reaching to the radiation detector 5 by Expressions (6) and (7) by using the primary ray transmittance Tp and the scattered ray transmittance Ts of the object interposed between the subject H and the radiation detector 5. Moreover, a sum Iw1 of the primary ray distribution Ip1 and the scattered ray distribution Is1 is derived by Expression (8). Also in Expressions (6) and (7), the initial body thickness distribution t0 is used as the body thickness distribution t in a case of first derivation of the first primary ray distribution Ip0 and the scattered ray distribution Is1.

$$Ip1 = Ip0 \times Tp(kV(,mmAl),t) \quad (6)$$

$$Is1 = Is0 \times Ts(kV(,mmAl),t) \quad (7)$$

$$Iw1 = Ip1 + Is1 \quad (8)$$

The calculation unit 26 derives an error E2 between the sum Iw1 of the primary ray distribution Ip1 and the scattered ray distribution Is1 and the dose at each pixel position of the radiation image G0, that is, a pixel value H. The derivation of the error E2 is performed by Expression (9) or Expression (9-1). In Expressions (9) and (9-1), N represents the number of pixels of the radiation image G0 and Σ represents a sum of all of the pixels of the radiation image G0. Note that, since in Expression (9-1), I1/Iw1 is calculated in the log, the error E2 can be derived without depending on the emitted dose to the subject H, that is, the reaching dose I0.

$$E2=(1/N)\times\Sigma\{I1-Iw1\}^2 \quad (9)$$

$$E2=(1/N)\times\Sigma|\log\{I1/Iw1\}| \quad (9\text{-}1)$$

Moreover, the calculation unit 26 updates the body thickness distribution t such that the error E2 is minimized or the error E2 is smaller than a predetermined threshold value Th2. Moreover, the calculation unit 26 repeats the acquisition of the primary ray transmittance Tp and the scattered ray transmittance Ts based on the updated body thickness distribution, and the derivation of the primary ray distribution Ip1 and the scattered ray distribution Is1. Here, the calculation performed by the calculation unit 26 is referred to as a repetitive calculation. In addition, in the present embodiment, the calculation unit 26 repeatedly performs the repetitive calculation such that the error E2 is smaller than the predetermined threshold value Th2. Moreover, the calculation unit 26 outputs the processed radiation image Gm which uses, as the pixel value, the primary ray distribution Ipm derived based on the body thickness distribution tm of the subject H in which the error E2 is smaller than the predetermined threshold value Th2.

Note that the characteristic acquisition unit 24 and the ray distribution derivation unit 25 perform the repetitive acquisition of the primary ray transmittance Tp and the scattered ray transmittance Ts and the repetitive derivation of the primary ray distribution Ip1 and the scattered ray distribution Is1, respectively. Repetitive calculation processing performed by the calculation unit 26 will be described below.

The display controller 27 displays the processed radiation image Gm on the display unit 8.

Figure 9:
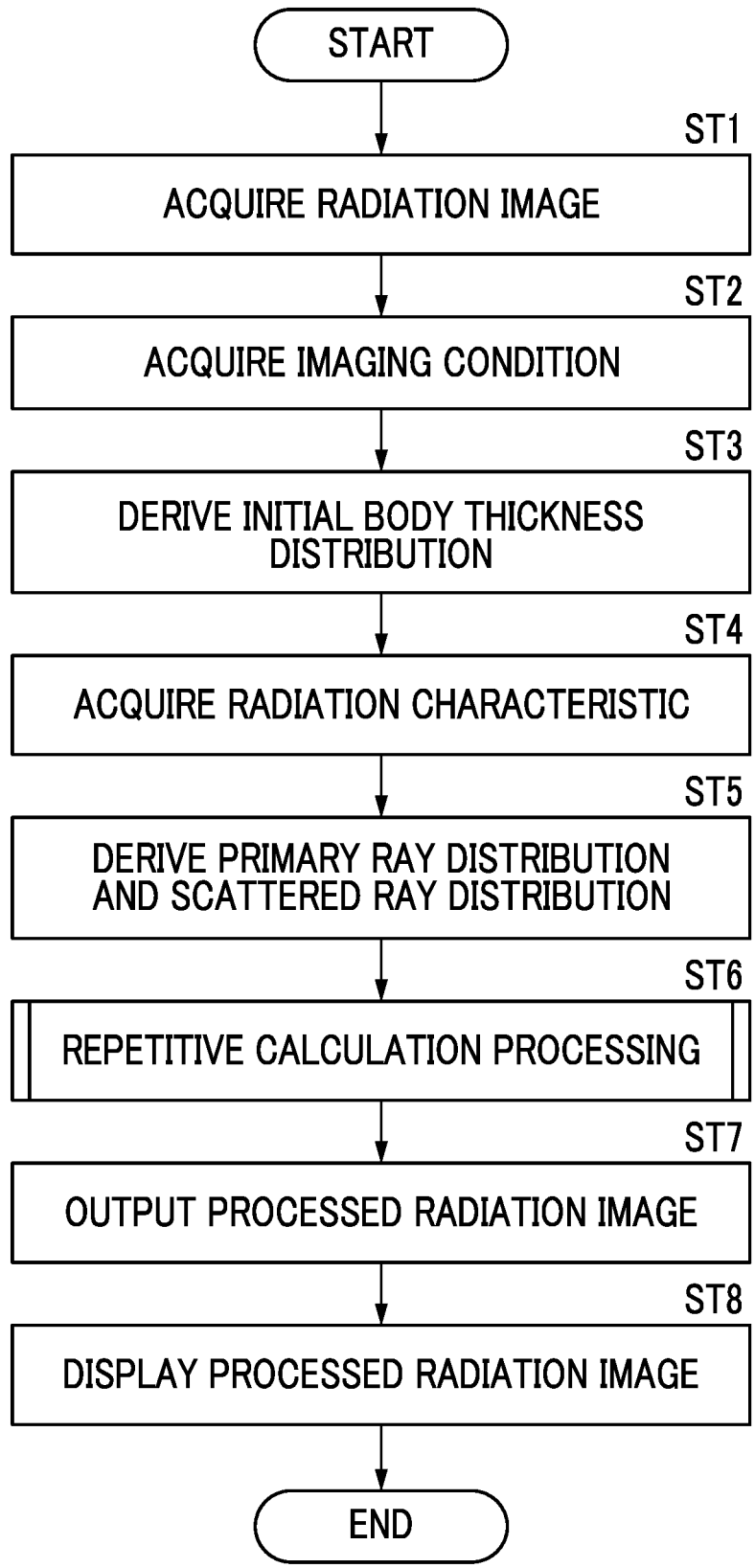
FIG. 9 is a flowchart showing processing performed in the first embodiment.

Then, processing performed in the first embodiment will be described. FIG. 9 is a flowchart showing the processing performed in the first embodiment. Note that the radiation image G0 is acquired by imaging and stored in the storage 13. In a case in which an instruction for starting the processing is input from the input unit 9, the image acquisition unit 21 acquires the radiation image G0 from the storage 13 (step ST1). Then, the imaging condition acquisition unit 22 acquires the imaging conditions in a case in which the subject H is imaged in the imaging apparatus 1 (step ST2). Then, the body thickness derivation unit 23 derives the initial body thickness distribution t0 based on the radiation image G0 and the imaging conditions (step ST3). Further, the characteristic acquisition unit 24 acquires the radiation characteristic of the object interposed between the subject H and the radiation detector 5 at the time of imaging, that is, the primary ray transmittance Tp and the scattered ray transmittance Ts (step ST4). Subsequently, the ray distribution derivation unit 25 derives the primary ray distribution Ip1 and the scattered ray distribution Is1 of the radiation detected by the radiation detector 5 by using the imaging conditions, the body thickness distribution, and the radiation characteristic of the object interposed between the subject H and the radiation detector 5 (step ST5). As described above, the processing of steps ST3 to ST5 is performed based on the initial body thickness distribution t0.

Figure 10:
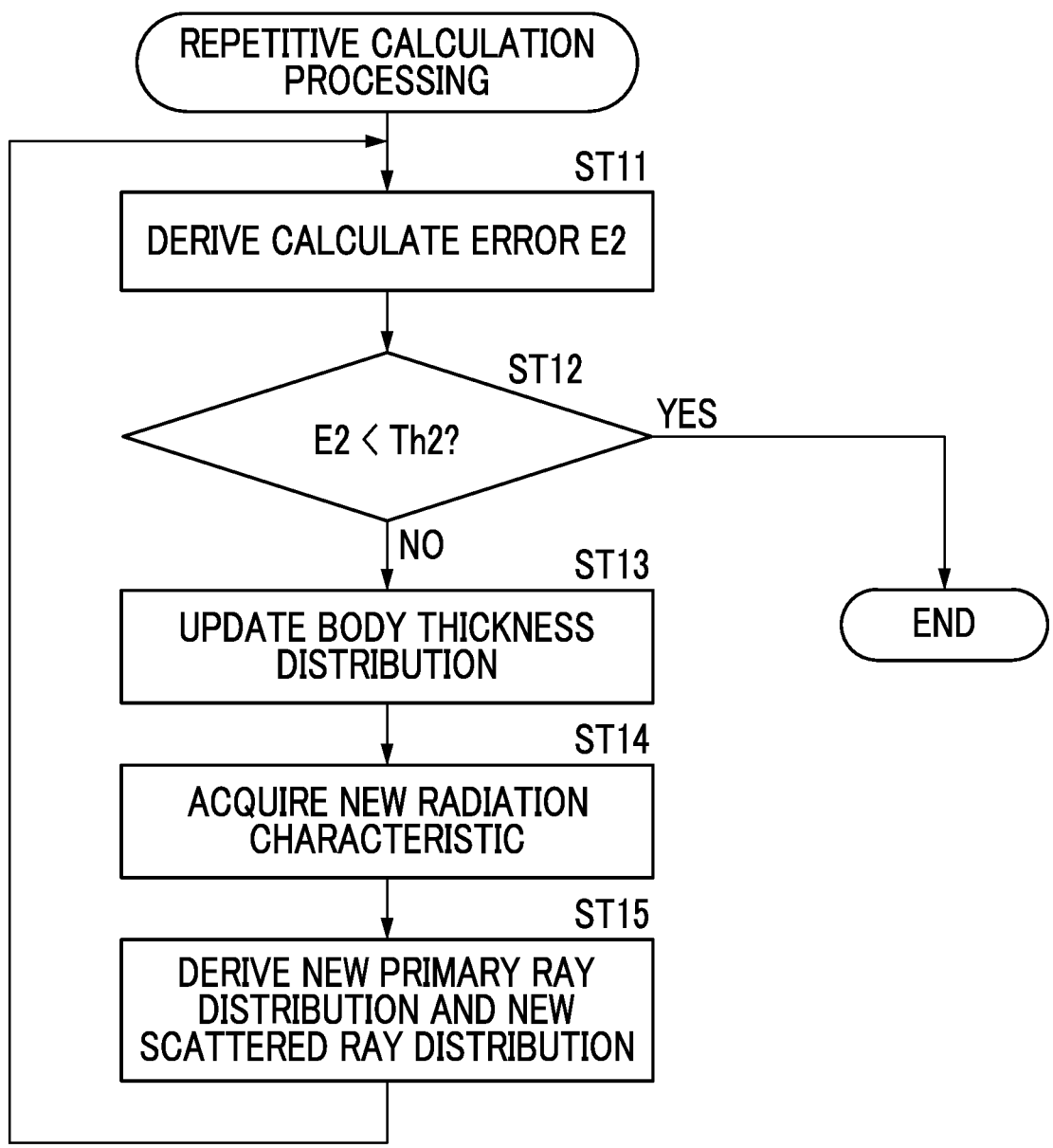
FIG. 10 is a flowchart of repetitive calculation processing.

Then, the calculation unit 26 performs repetitive calculation processing (step ST6). FIG. 10 is a flowchart of the repetitive calculation processing. First, the calculation unit 26 derives the error E2 between the sum Iw1 of the primary ray distribution Ip1 and the scattered ray distribution Is1 and the pixel value I1 at each position of the radiation image G0 (step ST11). Moreover, the calculation unit 26 determines whether or not the error E2 is smaller than the predetermined threshold value Th2 (step ST12). In a case in which a negative determination is made in step ST12, the body thickness distribution t is updated such that the error E2 is small (step ST13). Moreover, the characteristic acquisition unit 24 acquires a new radiation characteristic, that is, the primary ray transmittance Tp and the scattered ray transmittance Ts, based on the updated body thickness distribution t (step ST14). In addition, the ray distribution derivation unit 25 derives the new primary ray distribution Ip1 and the scattered ray distribution Is1 (step ST15). Moreover, the calculation unit 26 returns to the processing of step ST11 and repeats the processing of steps ST11 to ST15. In a case in which a positive determination is made in step ST12, the repetitive calculation processing is terminated.

Returning to FIG. 9, in a case in which the repetitive calculation processing is terminated, the calculation unit 26 outputs the processed radiation image Gm including, as the pixel value, the primary ray distribution Ipm derived based on the body thickness distribution tm of the subject H in which the error E2 is smaller than the predetermined threshold value Th2 (step ST7). Moreover, the display controller 27 displays the processed radiation image Gm on the display unit 8 (step ST8), and the processing is terminated.

As described above, in the first embodiment, the body thickness distribution of the subject H is derived based on the radiation image G0 and the imaging conditions, and the primary ray distribution Ip1 and the scattered ray distribution Is1 of the radiation detected by the radiation detector 5 are derived by using the imaging condition, the body thickness distribution t, and the radiation characteristic of the object. Moreover, the error E2 between the sum Iw1 of the primary ray distribution Ip1 and the scattered ray distribution Is1 and the pixel value at each position of the radiation image G0 is derived, the body thickness distribution is updated such that the error E2 is smaller than the predetermined threshold value Th2, and the acquisition of the radiation characteristic based on the updated body thickness distribution and the derivation of the primary ray distribution and the scattered ray distribution are repeated. Therefore, the primary ray distribution Ip1 and the scattered ray distribution Is1 can be derived in consideration of the radiation characteristic of the object interposed between the subject H and the radiation detector 5. Since the primary ray distribution Ip1 derived in this way takes into consideration the radiation characteristic of the object interposed between the subject H and the radiation detector 5, the scattered ray component is removed with high accuracy. Therefore, according to the first embodiment, it is possible to acquire the processed radiation image Gm from which the scattered ray component is removed with high accuracy in consideration of the object interposed between the subject H and the radiation detector 5.

Figure 11:
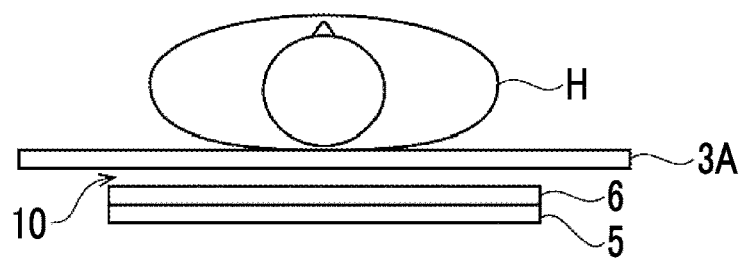
FIG. 11 is a diagram showing a state in which an air layer is interposed between a top plate and a grid.

Note that, in the first embodiment, the top plate 3A and the grid 6 of the imaging table 3 are used as the object interposed between the subject H and the radiation detector 5, but as shown in FIG. 11, an air layer 10 may be interposed between the top plate 3A and the grid 6. In such a case, it is preferable that the ray distribution derivation unit 25 derive the primary ray distribution Ip1 and the scattered ray distribution Is1 by including the air layer 10 as the object interposed between the subject H and the radiation detector 5. In this case, as shown in Expressions (6-1) and (7-1), the primary ray distribution Ip1 and the scattered ray distribution Is1 need only be derived by performing convolution operation on a point spread function PSFair(kV(, mmAl), tair) depending on the thickness tair of the air layer 10 with respect to Expressions (6) and (7). Note that the thickness tair of the air layer 10 is the distance between the lower surface of the top plate 3A and the surface of the grid 6 on the subject H side.

$$Ip1=Ip0 \times Tp(kV(,mmAl),t)*PSF_{air}(kV(,mmAl),t_{air}) \qquad (6\text{-}1)$$

$$Is1=Is0 \times Ts(kV(,mmAl),t)*PSF_{air}(kV(,mmAl),t_{air}) \qquad (7\text{-}1)$$

Figure 12:
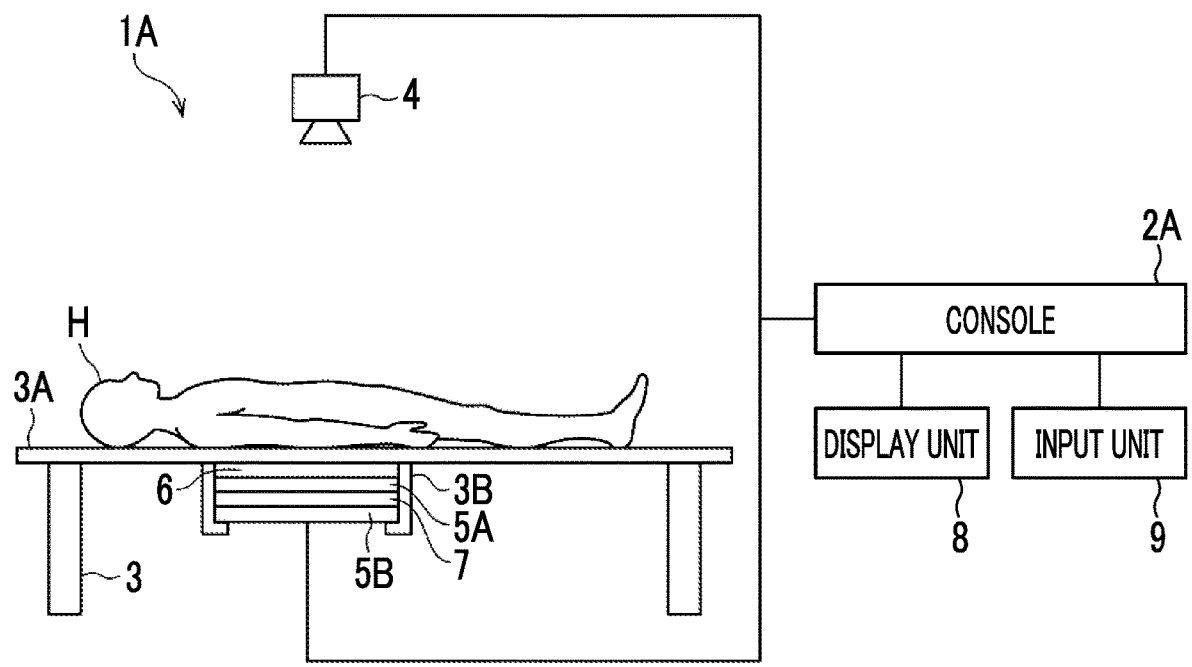
FIG. 12 is a schematic block diagram showing a configuration of a radiography system to which a radiation image processing device according to a second embodiment of the present disclosure is applied.

Then, a second embodiment of the present disclosure will be described. FIG. 12 is a schematic block diagram showing a configuration of a radiography system to which a radiation image processing device according to the second embodiment of the present disclosure is applied. Note that, in FIG. 12, the same components as those in FIG. 1 are denoted by the same references, and detailed description is omitted. As shown in FIG. 12, the radiography system according to the second embodiment is a system that captures two radiation images having different energy distributions and performs the energy subtraction processing by using the two radiation images, and comprises an imaging apparatus 1A and a console 2A that encompasses the radiation image processing device according to the second embodiment. The imaging apparatus 1A comprises a first radiation detector 5A and a second radiation detector 5B.

The imaging apparatus 1A according to the second embodiment is an imaging apparatus that performs a so-called one-shot energy subtraction for converting the radiation emitted from a radiation source 4 and transmitted through the subject H into energy and irradiating the first radiation detector 5A and the second radiation detector 5B with the converted radiation. At the time of imaging, as shown in FIG. 12, the first radiation detector 5A, a radiation energy conversion filter 7 made of a copper plate or the like, and the second radiation detector 5B are disposed in order from a side closest to the radiation source 4, and the radiation source 4 is driven. Note that the first and second radiation detectors 5A and 5B are closely attached to the radiation energy conversion filter 7. Note that the grid 6 is disposed on the subject H side of the first radiation detector 5A as in the first embodiment.

As a result, in the first radiation detector 5A, a first radiation image G1 of the subject H by low-energy radiation including so-called soft rays is acquired. In addition, in the second radiation detector 5B, a second radiation image G2 of the subject H by high-energy radiation from which the soft rays are removed is acquired. The first and second radiation images are input to the console 2A.

Figure 13:
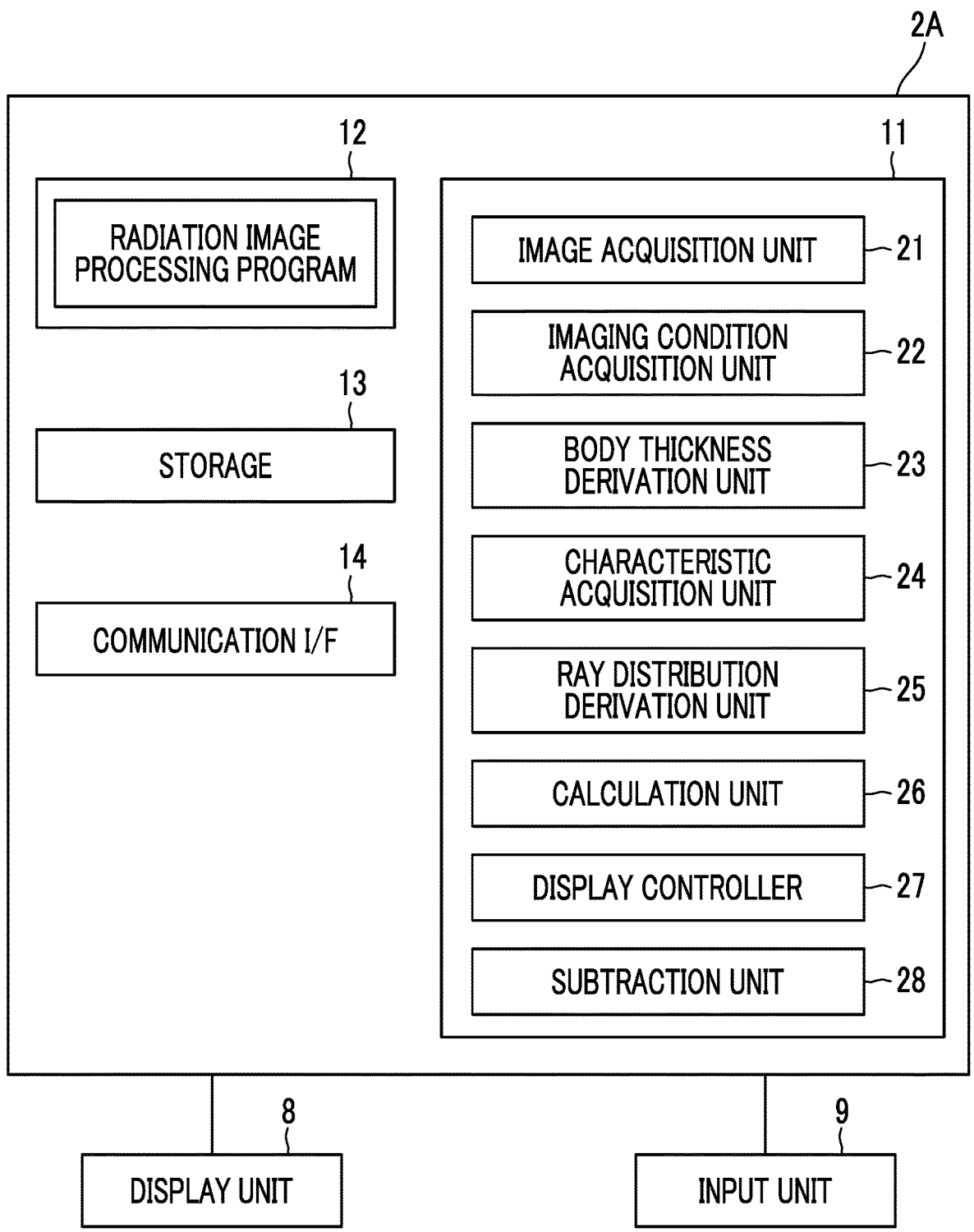
FIG. 13 is a diagram showing a schematic configuration of the radiation image processing device according to the second embodiment.

FIG. 13 is a diagram showing a schematic configuration of the radiation image processing device according to the second embodiment, which is realized by installing the radiation image processing program according to the second embodiment on the computer configuring the console 2A. Note that, in FIG. 13, the same components as those in FIG. 2 are denoted by the same references, and detailed description is omitted. As shown in FIG. 13, the radiation image processing device according to the second embodiment is different from the first embodiment in that a subtraction unit 28 is provided.

Specifically, as represented by Expressions (10) and (11), the subtraction unit 28 derives a soft part image Gs in which the soft part of the subject H is emphasized and a bone part image Gb in which the bone part is emphasized are derived by performing subtraction processing of performing weighting subtraction between the corresponding pixels of the first and second radiation images Gm1 and Gm2 from which the scattered ray component is removed as described below. In Expressions (10) and (11), α and β are weighting coefficients.

$$Gs=\alpha \cdot Gm2-Gm1 \qquad (10)$$

$$Gb=\beta \cdot Gm2-Gm1 \qquad (11)$$

Figure 14:
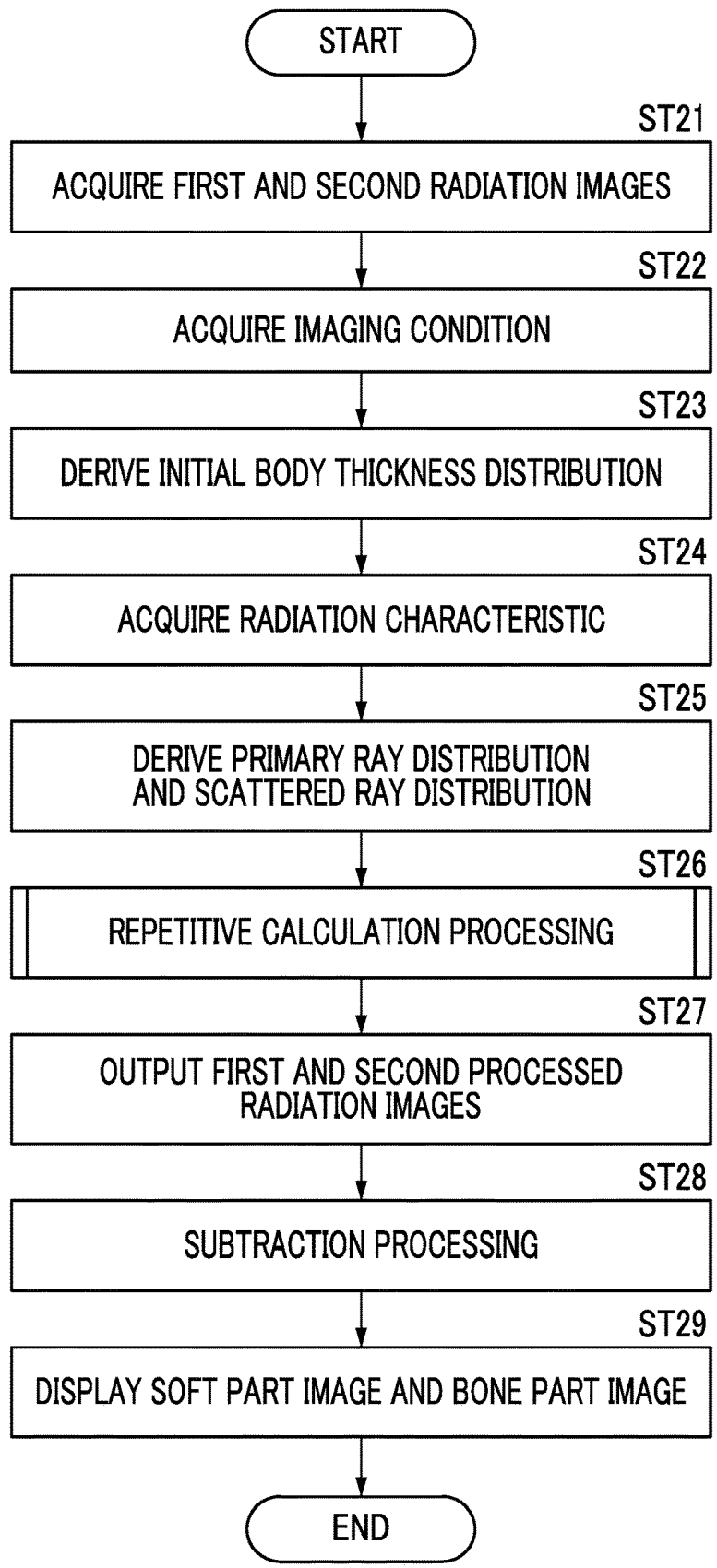
FIG. 14 is a flowchart showing processing performed in the second embodiment.

Then, processing performed in the second embodiment will be described. FIG. 14 is a flowchart showing the processing performed in the second embodiment. Note that the first and second radiation images G1 and G2 are acquired by imaging and stored in the storage 13. In a case in which an instruction for starting the processing is input from the input unit 9, the image acquisition unit 21 acquires the first and second radiation images G1 and G2 from the storage 13 (step ST21). Then, the imaging condition acquisition unit 22 acquires the imaging conditions in a case in which the subject H is imaged in the imaging apparatus 1 (step ST22). Then, the body thickness derivation unit 23 derives the initial body thickness distribution t0 based on the first radiation image G1 or the second radiation image G2 and the imaging conditions (step ST23). Further, the characteristic acquisition unit 24 acquires the radiation characteristic of the object interposed between the subject H and the radiation detector 5 at the time of imaging, that is, the primary ray transmittance Tp and the scattered ray transmittance Ts (step ST24). Subsequently, the ray distribution derivation unit 25 derives the primary ray distributions Ip1-1 and Ip1-2 and the scattered ray distributions Is1-1 and Is1-2 of the radiation detected by the first and second radiation detectors 5A and 5B, respectively, by using the imaging conditions, the body thickness distribution, and the radiation characteristic of the object interposed between the subject H and the radiation detector 5 (step ST25). As described above, the processing of steps ST23 to ST25 is performed based on the initial body thickness distribution t0.

Then, the calculation unit 26 performs repetitive calculation processing (step ST26). In the second embodiment, the repetitive calculation is performed by using each of the primary ray distribution Ip1-1 and the scattered ray distribution Is1-1 detected by the first radiation detector 5A, and the primary ray distribution Ip1-2 and the scattered ray distribution Is1-2 detected by the second radiation detector 5B. That is, for each of the first radiation image G1 and the second radiation image G2, the primary ray distribution Ipm-1 and the primary ray distribution Ipm-2 are derived based on the body thickness distribution tm of the subject H in which the error E2 is smaller than the predetermined threshold value Th2.

In a case in which the repetitive calculation processing is terminated, the calculation unit 26 outputs a first processed radiation image Gm1 and a second processed radiation image Gm2 including, as the pixel value, the primary ray distribution Ipm-1 and the primary ray distribution Ipm-2, respectively, derived based on the body thickness distribution tm of the subject H in which the error E2 is smaller than the predetermined threshold value Th2 (step ST27). Moreover, the subtraction unit 28 performs the subtraction processing (step ST28). As a result, the soft part image Gs and the bone part image Gb are derived. Moreover, the display controller 27 displays the soft part image Gs and the bone part image Gb on the display unit 8 (step ST29), and the processing is terminated.

As described above, in the second embodiment, the subtraction processing is performed by using the first and second processed radiation images Gm1 and Gm2 from which the scattered ray component is removed with high accuracy. Therefore, it is possible to derive the high-quality soft part image Gs and bone part image Gb from which the scattered ray component is removed.

Figure 15:
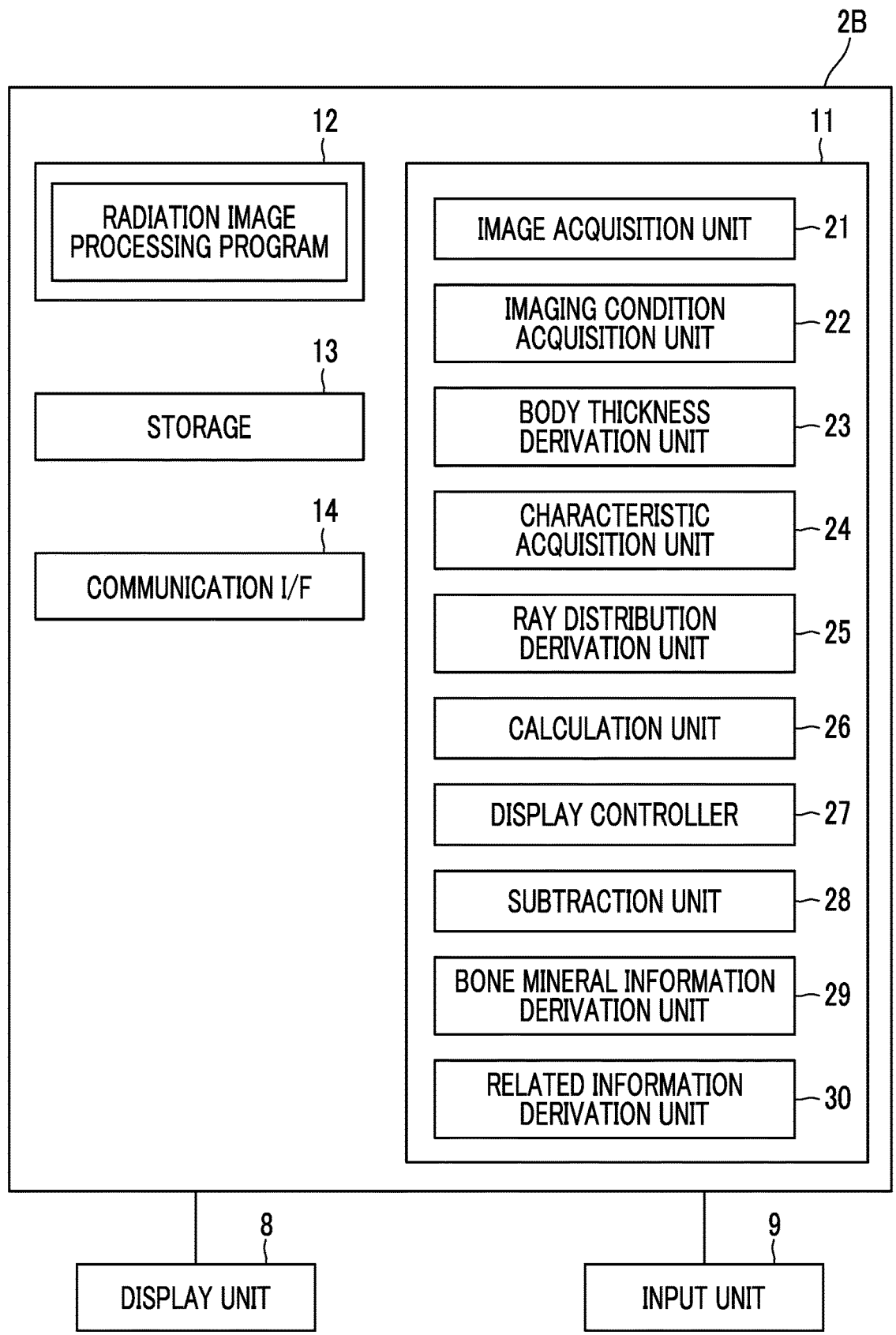
FIG. 15 is a diagram showing a schematic configuration of a radiation image processing device according to a third embodiment.

Then, a third embodiment of the present disclosure will be described. FIG. 15 is a diagram showing a schematic configuration of the radiation image processing device according to the third embodiment, which is realized by installing the radiation image processing program according to the third embodiment on the computer configuring a console 2B. Note that, in FIG. 15, the same components as those in FIG. 13 are denoted by the same references, and detailed description is omitted. As shown in FIG. 15, the radiation image processing device according to the third embodiment is different from the second embodiment in that a bone mineral information derivation unit 29 and a related information derivation unit 30 are provided in addition to the subtraction unit 28 of the radiation image processing device according to the second embodiment.

The bone mineral information derivation unit 29 acquires bone mineral information representing a bone mineral density in the bone region for each pixel of the bone region included in the first and second radiation images G1 and G2. In the third embodiment, the bone mineral information derivation unit 29 derives the bone mineral information by converting the pixel value of the bone region into the pixel value of the bone part image acquired under a standard imaging condition.

Figure 16:
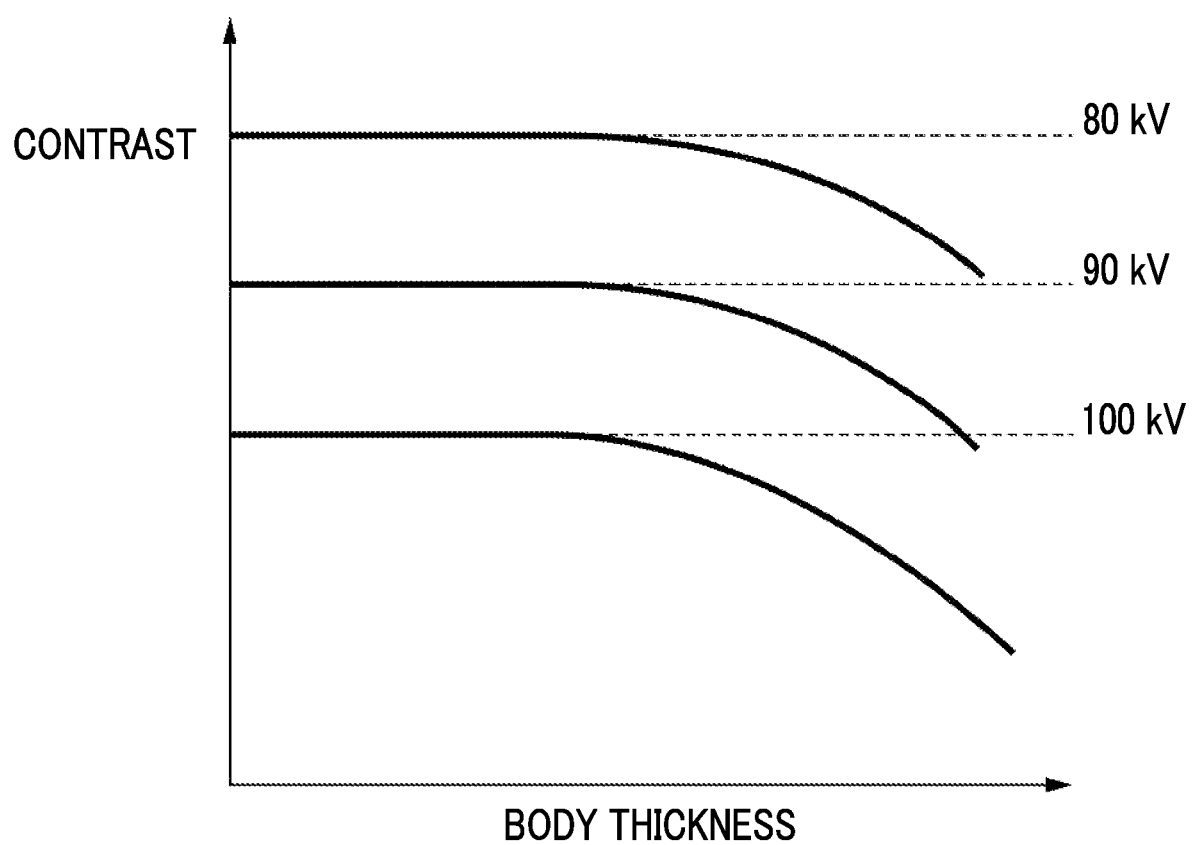
FIG. 16 is a diagram showing a relationship between the contrast of a bone part and a soft part and the body thickness.

Here, a contrast between the soft part and the bone part in the acquired radiation image is lower as the tube voltage applied to the radiation source 4 is higher and the energy of the radiation is higher. In addition, in a procedure of the radiation transmitted through the subject H, a low-energy component of the radiation is absorbed by the subject H, and beam hardening occurs in which the X-ray energy is increased. The increase in the X-ray energy due to the beam hardening is larger as the body thickness of the subject H is larger. FIG. 16 is a diagram showing a relationship of the contrast between the bone part and the soft part with respect to the body thickness. Note that FIG. 16 shows the relationship of the contrast between the bone part and the soft part with respect to the body thickness at the three tube voltages of 80 kV, 90 kV, and 100 kV. As shown in FIG. 16, the contrast is lower as the tube voltage is higher. In addition, in a case in which the body thickness exceeds a certain value, the contrast is lower as the body thickness is larger. Note that the contrast between the bone part and the soft part is higher as the pixel value of the bone region in the bone part image Gb is larger. Therefore, the relationship shown in FIG. 16 shifts to a higher contrast side as the pixel value of the bone region in the bone part image Gb derived by the subtraction processing is increased.

Figure 17:
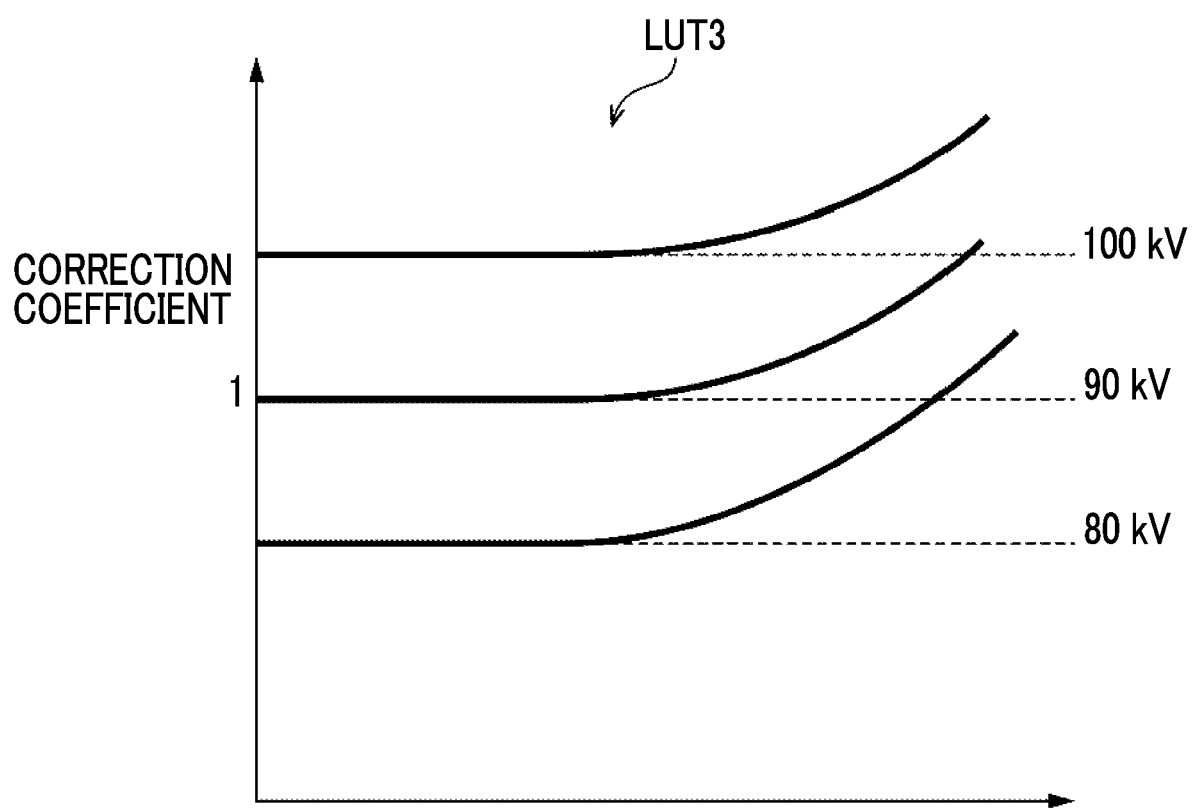
FIG. 17 is a diagram showing an example of a look-up table for acquiring a correction coefficient.

In the third embodiment, a look-up table in which the standard imaging condition is set to the tube voltage of 90 kV is prepared. The look-up table is used for acquiring the correction coefficient for correcting the difference in the contrast depending on the tube voltage at the time of imaging and the reduction in the contrast due to the influence of the beam hardening. Note that the look-up table is stored in the storage 13. FIG. 17 is a diagram showing the look-up table for acquiring the correction coefficient. As shown in FIG. 17, in the look-up table LUT3, the value of the correction coefficient is larger as the tube voltage is higher and the body thickness is larger. Note that, in the third embodiment, since the standard imaging condition is the tube voltage of 90 kV, the correction coefficient is 1 in a case in which the tube voltage is 90 kV and the thickness is 0. In addition, although the look-up table LUT3 is shown in two dimensions in FIG. 17, the correction coefficient differs depending on the pixel value of the bone region. Therefore, the look-up table LUT3 is actually a three-dimensional table to which an axis representing the pixel value of the bone region is added.

The bone mineral information derivation unit 29 acquires a correction coefficient C0 for each pixel in accordance with the imaging condition and the body thickness distribution tm in which the error E2 is smaller than the threshold value Th2 with reference to the look-up table LUT3. The correction coefficient C0 is acquired for each pixel of the bone part image Gb. Moreover, as shown in Expression (12), the bone mineral information derivation unit 29 multiplies the pixel value Gb(x,y) of each pixel of the bone region in the bone part image Gb by the correction coefficient C0(x,y) to derive the bone mineral information B0(x,y) for each pixel of the bone region. The bone mineral information B0(x,y) derived in this way is acquired by imaging the subject by the tube voltage of 90 kV, which is the standard imaging condition, and represents the pixel value of the bone part in the bone region included in the radiation image from which the influence of the beam hardening is removed.

$$B0(x,y)=C0(x,y)\times Gb(x,y) \qquad (12)$$

The related information derivation unit 30 derives the related information, which is related to the bone mineral information. In the third embodiment, the related information derivation unit 30 derives a composite image Gc in which the bone mineral information B0 is superimposed on the soft part image Gs generated by the subtraction unit 28, as the related information. Note that, in the third embodiment, the bone mineral information B0 may be superimposed on the bone part image Gb to derive the composite image Gc, or the bone mineral information B0 may be superimposed on any of the first radiation image G1 or the second radiation image G2 to derive the composite image Gc.

Figure 18:
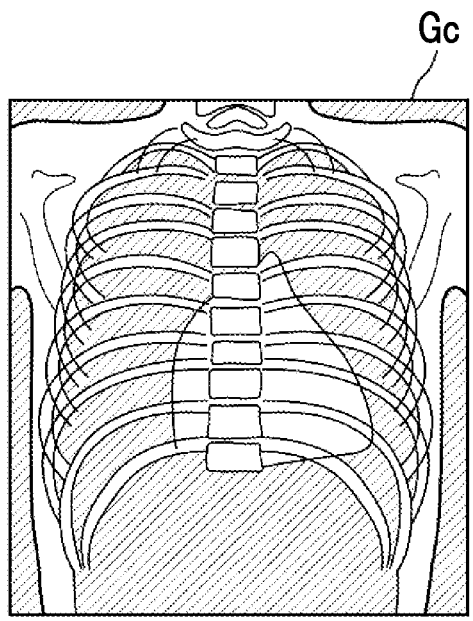
FIG. 18 is a diagram showing a composite image.

In the third embodiment, the display controller 27 displays the related information on the display unit 8. FIG. 18 is a diagram showing the related information displayed on the display unit 8. As shown in FIG. 18, the related information is the composite image Gc described above.

Figure 19:
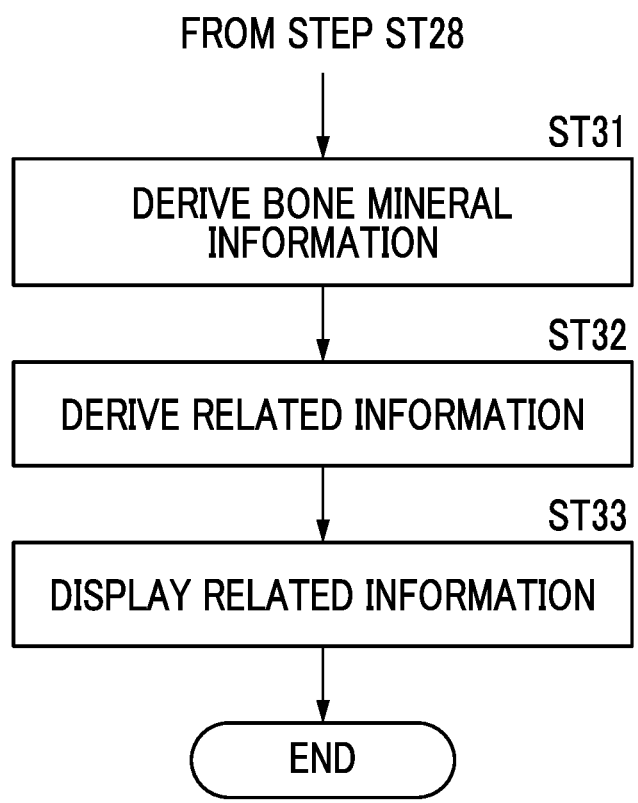
FIG. 19 is a flowchart showing processing performed in the third embodiment.

Then, processing performed in the third embodiment will be described. FIG. 19 is a flowchart showing the processing performed in the third embodiment. Note that, in the third embodiment, the processing up to the processing performed by the subtraction unit 28 is the same as the processing of steps ST21 to ST28 in the second embodiment shown in FIG. 14, and thus the processing after step ST28 in FIG. 14 will be described in FIG. 19. In a case in which the soft part image Gs and the bone part image Gb are generated in the processing of step ST28, the bone mineral information derivation unit 29 derives the bone mineral information representing the bone mineral density in the bone region for each pixel of the bone region based on the imaging conditions, the body thickness distribution, and the pixel value of the bone region in the bone part image Gb (step ST31). Further, the related information derivation unit 30 derives the related information, which is related to the bone mineral information (step ST32), the display controller 27 displays the related information on the display unit 8 (step ST33), and the processing is terminated.

As described above, in the third embodiment, the bone mineral information and the related information are derived by using the bone part image Gb acquired by performing the subtraction processing using the first and second processed radiation images Gm1 and Gm2 from which the scattered ray component is removed with high accuracy. Therefore, the bone mineral information and the related information can be acquired with high accuracy without being affected by the scattered ray component.

Figure 20:
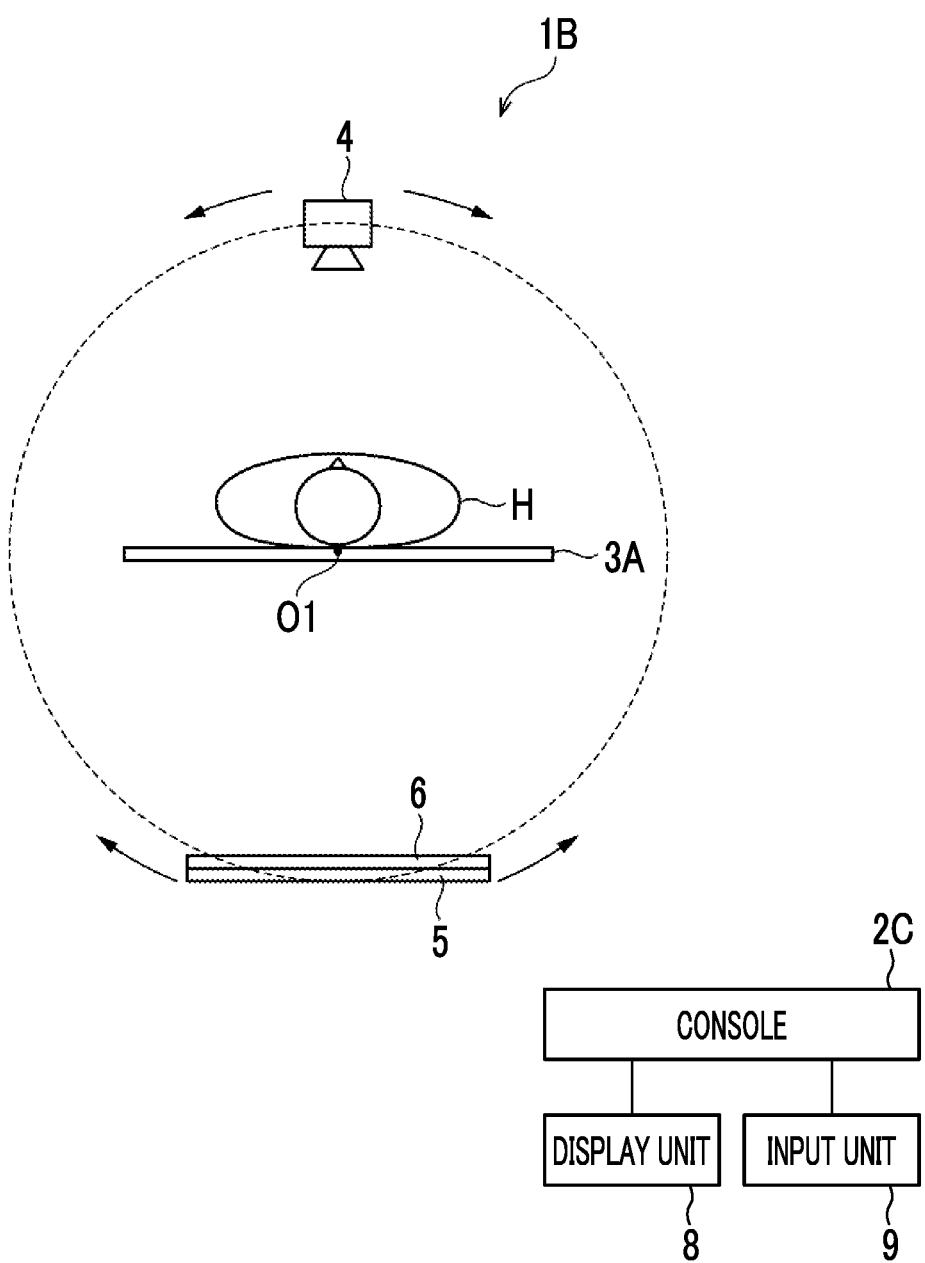
FIG. 20 is a schematic block diagram showing a configuration of a radiography system to which a radiation image processing device according to a fourth embodiment of the present disclosure is applied.

Then, a fourth embodiment of the present disclosure will be described. FIG. 20 is a schematic block diagram showing a configuration of a radiography system to which a radiation image processing device according to the fourth embodiment of the present disclosure is applied. Note that, in FIG. 20, the same components as those in FIG. 1 are denoted by the same references, and detailed description is omitted. As shown in FIG. 20, the radiography system according to the fourth embodiment comprises an imaging apparatus 1B and a console 2C that encompasses the radiation image processing device according to the fourth embodiment. The imaging apparatus 1B is the imaging apparatus 1B capable of generating a three-dimensional image, such as a cone beam CT disclosed in JP2000-139901A.

In the imaging apparatus 1B, the radiation source 4, the radiation detector 5, and the grid 6 are disposed at positions facing each other with the subject H on the top plate 3A of the imaging table 3 interposed therebetween. The radiation source 4, the radiation detector 5, and the grid 6 are integrally rotatable around a rotation center O1 of the top plate 3A by a driving unit (not shown). The imaging apparatus 1B images the subject H at a plurality of projection positions on a rotation orbit of the radiation source 4, the radiation detector 5, and the grid 6 to acquire a plurality of radiation images corresponding to the projection positions as projection images Pk (k=1 to n: n is the number of projection images). In the third embodiment, the acquired plurality of projection images Pk are input to the console 2C.

Figure 21:
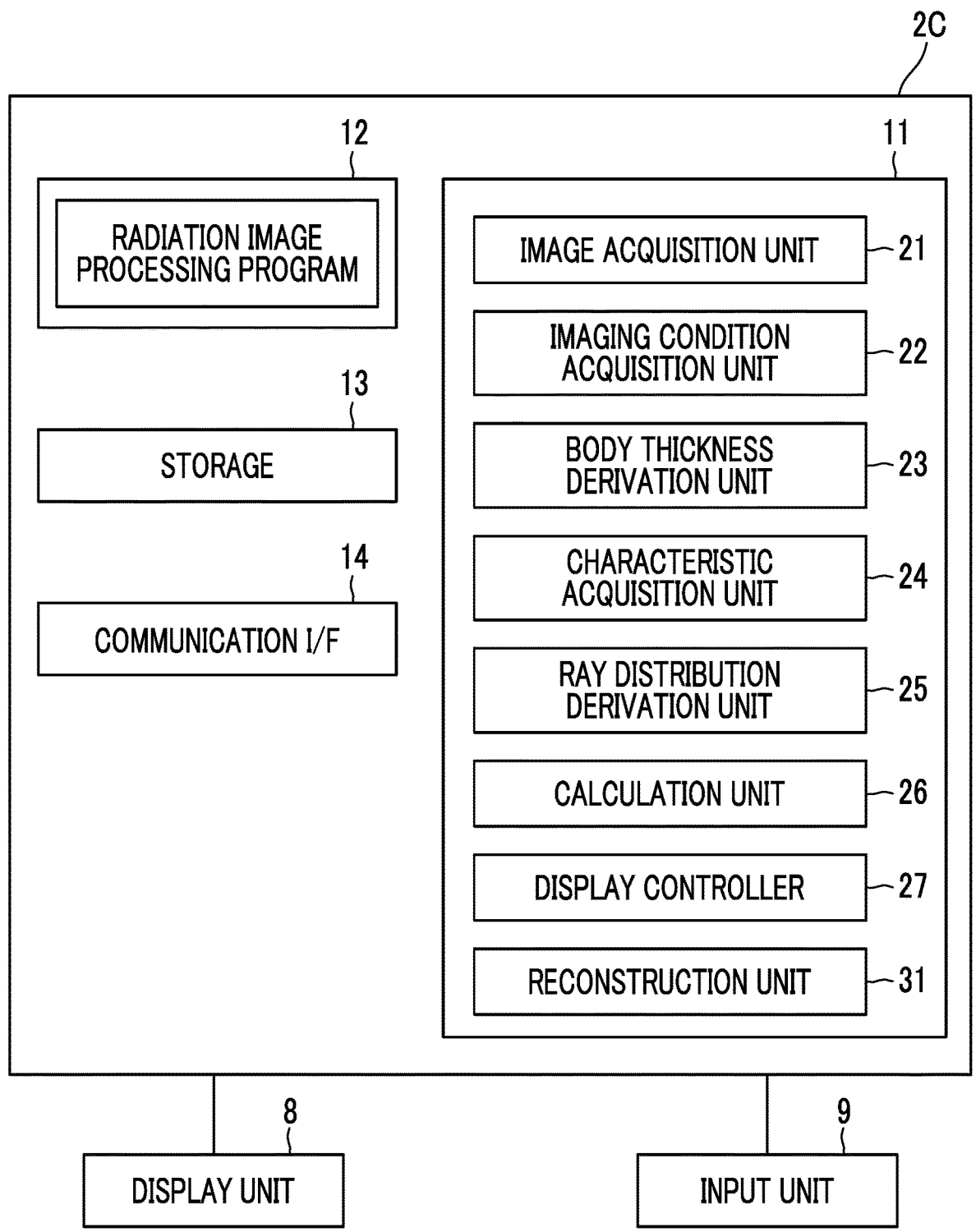
FIG. 21 is a diagram showing a schematic configuration of the radiation image processing device according to the fourth embodiment.

FIG. 21 is a diagram showing a schematic configuration of the radiation image processing device according to the fourth embodiment, which is realized by installing the radiation image processing program according to the fourth embodiment on the computer configuring the console 2C. Note that, in FIG. 21, the same components as those in FIG. 2 are denoted by the same references, and detailed description is omitted. As shown in FIG. 21, the radiation image processing device according to the fourth embodiment is different from the first embodiment in that a reconstruction unit 31 that reconstructs the plurality of projection images to generate a tomographic image of the subject H is provided.

The reconstruction unit 31 reconstructs the plurality of projection images Pk from which the scattered ray component is removed as described below to generate a plurality of tomographic images Dj (j=1 to m: m is the number of tomographic images) representing a plurality of tomographic planes of the subject H, respectively. As a reconstruction method, any method, such as a Feldkamp method and a Grangeat method, can be used.

Note that, in the fourth embodiment, the initial body thickness distribution t0 derived by the body thickness derivation unit 23 is derived based on the projection image acquired by imaging the subject H at a position at which the radiation source 4 faces the subject H, that is, a state shown in FIG. 21.

Figure 22:
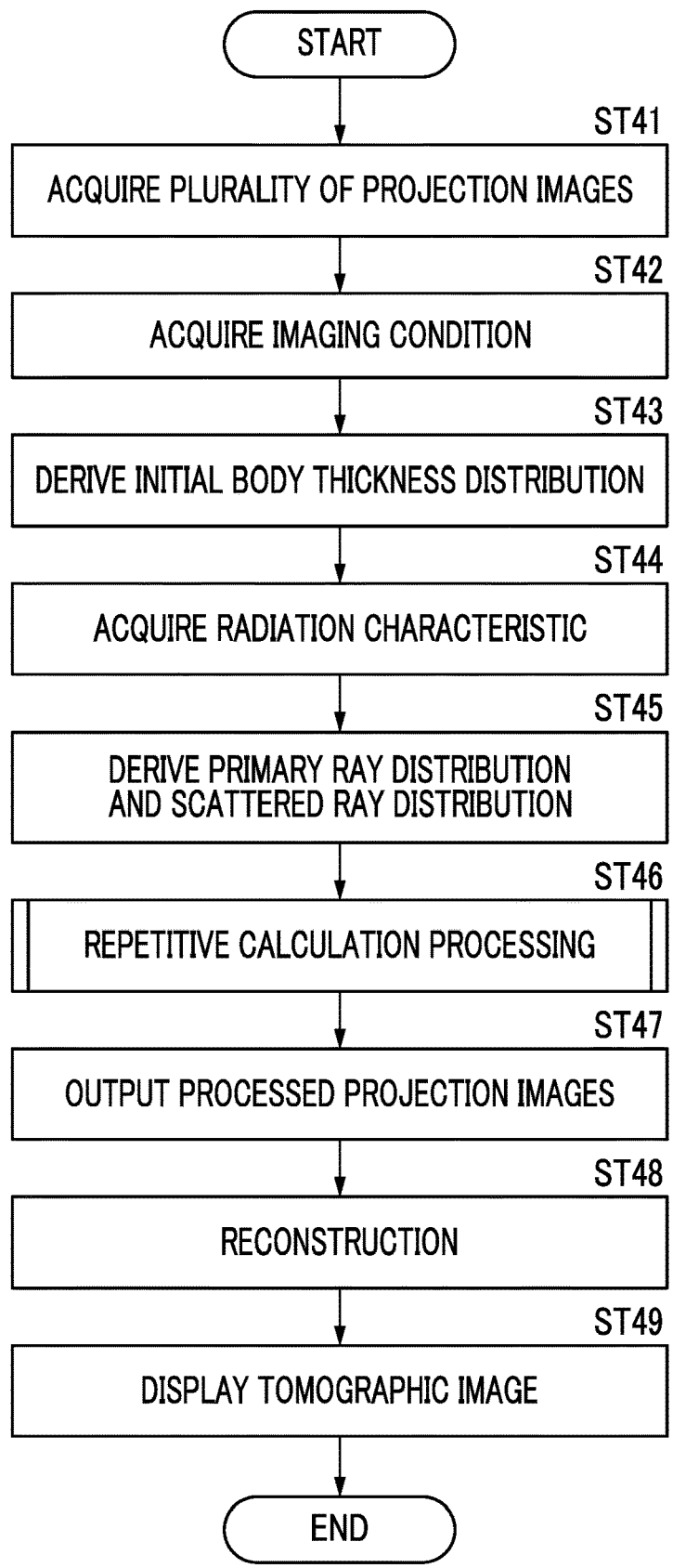
FIG. 22 is a flowchart showing processing performed in the fourth embodiment.

Then, processing performed in the fourth embodiment will be described. FIG. 22 is a flowchart showing the processing performed in the fourth embodiment. Note that the plurality of projection images Pk are acquired by imaging and stored in the storage 13. In a case in which an instruction for starting the processing is input from the input unit 9, the image acquisition unit 21 acquires the plurality of projection images Pk from the storage 13 (step ST41). Then, the imaging condition acquisition unit 22 acquires the imaging conditions in a case in which the subject H is imaged in the imaging apparatus 1 (step ST42). Then, the body thickness derivation unit 23 derives the initial body thickness distribution t0 based on the projection image acquired at the position at which the radiation source 4 faces the subject H and the imaging conditions (step ST43). Further, the characteristic acquisition unit 24 acquires the radiation characteristic of the object interposed between the subject H and the radiation detector 5 at the time of imaging, that is, the primary ray transmittance Tp and the scattered ray transmittance Ts (step ST44).

Note that, in the fourth embodiment, in addition to the grid 6, a relatively wide air layer is present between the subject H and the radiation detector 5. Therefore, the storage 13 stores a table representing a relationship between the body thickness distribution t, the primary ray transmittance Tp, and the scattered ray transmittance Ts in accordance with the thickness of the air layer in the imaging apparatus 1B. The characteristic acquisition unit 24 acquires the primary ray transmittance Tp and the scattered ray transmittance Ts with reference to the table.

Subsequently, the ray distribution derivation unit 25 derives the primary ray distribution Ip1-k and the scattered ray distribution Is1-k of the radiation detected by each of the plurality of projection images Pk by using the imaging conditions, the body thickness distribution, and the radiation characteristic of the object interposed between the subject H and the radiation detector 5 (step ST45). As described above, the processing of steps ST43 to ST45 is performed based on the initial body thickness distribution t0.

Then, the calculation unit 26 performs repetitive calculation processing (step ST46). In the fourth embodiment, the repetitive calculation is performed on the primary ray distribution Ip1-k and the scattered ray distribution Is1-k for each of the plurality of projection images Pk.

In a case in which the repetitive calculation processing is terminated, the calculation unit 26 outputs a processed projection image Pmk including, as the pixel value, the primary ray distribution Ipm-k derived based on the body thickness distribution tm of the subject H in which the error E2 is smaller than the predetermined threshold value Th2 (step ST47). Moreover, the reconstruction unit 31 reconstructs a plurality of processed projection images Pmk (step ST48). As a result, the tomographic image Dj for each of the plurality of tomographic planes of the subject H is derived. Moreover, the display controller 27 displays the tomographic image Dj on the display unit 8 (step ST49), and the processing is terminated.

As described above, in the fourth embodiment, the reconstruction processing is performed by using the plurality of processed projection images Pmk from which the scattered ray component is removed with high accuracy to generate the plurality of tomographic images Dj. Therefore, it is possible to derive the high-quality tomographic image Dj from which the scattered ray component is removed.

Note that, although the first and second radiation images G1 and G2 are acquired by one-shot method in the second and third embodiments described above, the first and second radiation images G1 and G2 may be acquired by a so-called two-shot method of performing imaging twice. In this case, the imaging condition acquisition unit 22 acquires both the imaging conditions in a case in which the first radiation image G1 is acquired and the imaging conditions in a case in which the second radiation image G2 is acquired. Moreover, the first processed radiation image Gm1 is acquired based on the imaging conditions in a case in which the first radiation image G1 is acquired, and the second processed radiation image Gm2 is acquired based on the imaging conditions in a case in which the second radiation image G2 is acquired.

In addition, in a case of the two-shot method, a position of the subject H included in the first radiation image G1 and the second radiation image G2 may shift due to a body movement of the subject H. Therefore, in the first radiation image G1 and the second radiation image G2, it is preferable to perform the processing according to the present embodiment after registration of the subject is performed. As registration processing, for example, a method disclosed in JP2011-255060A can be used. In the method disclosed in JP2011-255060A, for each of the first and second radiation images G1 and G2, a plurality of first band images and a plurality of second band images representing structures having different frequency bands are generated, a misregistration amount of the positions corresponding to each other in the first band image and the second band image of the corresponding frequency band is acquired, and the registration of the first radiation image G1 and the second radiation image G2 is performed based on the misregistration amount.

In addition, in the fourth embodiment, the imaging apparatus 1B, such as a cone beam CT, is used to remove the scattered ray component in the plurality of projection images for generating the tomographic image, but the generation of the tomographic image is not limited to the cone beam CT. For example, the technology of the present disclosure can be applied to a case in which tomosynthesis imaging of moving the radiation source parallel to the radiation detector, acquiring the plurality of projection images by imaging the subject at a plurality of source positions, and reconstructing the projection images by using a back projection method, such as a simple back projection method or a filter back projection method, or a sequential reconstruction method to generate the tomographic image is performed. In this case, the acquired projection image need only be subjected to processing of removing the scattered ray component in the same manner as in the fourth embodiment.

In addition, in each of the embodiments described above, imaging is performed by using the grid 6, but the present disclosure is not limited to this. The technology of the present disclosure can be applied even in a case in which imaging is performed without using the grid 6. In this case, the object interposed between the subject H and the radiation detector 5 is the grid 6, or the grid 6 and the air layer. Therefore, a table that defines the relationship between the body thickness distribution of the subject H and the primary ray transmittance Tp and the scattered ray transmittance Ts need only be acquired in a situation in which the grid 6 is not used in the same manner as in each of the embodiments described above and stored in the storage 13.

In addition, in each of the embodiments described above, the image processing is performed by using the radiation image acquired by the system that captures the radiation image of the subject H by using the radiation detector 5, and the first and second radiation detectors 5A and 5B, but it is needless to say that the present disclosure can also be applied to a case in which the radiation image G0, and the first and second radiation images G1 and G2 are acquired by using an accumulative phosphor sheet. In this case, in the second and third embodiments, the first and second radiation images G1 and G2 need only be acquired by stacking two accumulative phosphor sheets, emitting the radiation transmitted through the subject H, accumulating and recording radiation image information of the subject H in each of the accumulative phosphor sheets, and photoelectrically reading the radiation image information from each of the accumulative phosphor sheets.

In addition, the radiation in each of the embodiments described above is not particularly limited, and α-rays or γ-rays can be applied in addition to the X-rays.

In addition, in the embodiments described above, as the hardware structure of the processing unit that executes various pieces of processing, such as the image acquisition unit 21, the imaging condition acquisition unit 22, the body thickness derivation unit 23, the characteristic acquisition unit 24, the ray distribution derivation unit 25, the calculation unit 26, the display controller 27, the subtraction unit 28, the bone mineral information derivation unit 29, the related information derivation unit 30, and the reconstruction unit 31 of the consoles 2, 2A, 2B, and 2C which are the radiation image processing devices, various processors as described below can be used. As described above, the various processors include, in addition to the CPU that is a general-purpose processor which executes software (program) and functions as various processing units, a programmable logic device (PLD) that is a processor whose circuit configuration can be changed after manufacture, such as a field programmable gate array (FPGA), and a dedicated electric circuit that is a processor having a circuit configuration which is designed for exclusive use in order to execute a specific processing, such as an application specific integrated circuit (ASIC).

One processing unit may be configured by one of these various processors, or may be a combination of two or more processors of the same type or different types (for example, a combination of a plurality of FPGAs or a combination of the CPU and the FPGA). In addition, a plurality of the processing units may be configured by one processor.

As an example of configuring the plurality of processing units by one processor, first, as represented by a computer, such as a client and a server, there is an aspect in which one processor is configured by a combination of one or more CPUs and software and this processor functions as a plurality of processing units. Second, as represented by a system on chip (SoC) or the like, there is an aspect of using a processor that realizes the function of the entire system including the plurality of processing units by one integrated circuit (IC) chip. In this way, as the hardware structure, the various processing units are configured by using one or more of the various processors described above.

Moreover, as the hardware structures of these various processors, more specifically, it is possible to use an electrical circuit (circuitry) in which circuit elements, such as semiconductor elements, are combined.

What is claimed is:

1. A radiation image processing device comprising:
at least one processor,
wherein the processor is configured to
acquire an imaging condition in a case in which a radiation image of a subject is acquired by a radiation detector detecting radiation transmitted through the subject in a state in which an object is interposed between the subject and the radiation detector,
derive a body thickness distribution of the subject based on the radiation image and the imaging condition,
derive a radiation characteristic of the object based on the body thickness distribution,
derive a primary ray distribution and a scattered ray distribution of the radiation detected by the radiation detector by using the imaging condition, the body thickness distribution, and the radiation characteristic of the object, and derive an error between a sum of the primary ray distribution and the scattered ray distribution and a pixel value at each position of the radiation image, update the body thickness distribution such that the error is smaller than a predetermined threshold value, and repeat derivation of the radiation characteristic based on the updated body thickness distribution and derivation of the primary ray distribution and the scattered ray distribution.

2. The radiation image processing device according to claim 1, wherein the processor is configured to output a processed radiation image including, as a pixel value, the primary ray distribution derived based on the body thickness distribution of the subject in which the error is smaller than the threshold value.

3. The radiation image processing device according to claim 1, further comprising:

a storage unit that stores the radiation characteristic measured in advance by using an imaging system that acquires the radiation image, wherein the processor is configured to acquire the radiation characteristic stored in the storage unit.

4. The radiation image processing device according to claim 1, wherein the object is at least one of an imaging table on which the subject is placed, a top plate, a scattered ray removal grid, or an air layer.

5. The radiation image processing device according to claim 1, wherein the radiation characteristic is a primary ray transmittance and a scattered ray transmittance.

6. The radiation image processing device according to claim 1, wherein the processor is configured to acquire a processed radiation image for each of two radiation images based on radiation having different energy distributions and transmitted through the subject, and derive a subtraction image obtained by extracting a specific structure of the subject by performing weighting subtraction between corresponding pixels of two processed radiation images.

7. The radiation image processing device according to claim 1, wherein the processor is configured to acquire a processed radiation image for each of two radiation images based on radiation having different energy distributions and transmitted through a subject including a bone part and a soft part, derive a bone part image obtained by extracting the bone part of the subject by performing weighting subtraction between corresponding pixels of two processed radiation images, and derive bone mineral information representing a bone mineral density in a bone region in the bone part image for each pixel of the bone region based on the imaging condition, the body thickness distribution, and a pixel value of the bone region.

8. The radiation image processing device according to claim 1, wherein the processor is configured to irradiate the subject with the radiation from a plurality of projection angles to acquire a processed radiation image for each of a plurality of radiation images corresponding to each of the plurality of projection angles, and reconstruct a plurality of the processed radiation images to generate a tomographic image of the subject.

9. A radiation image processing method comprising:

acquiring an imaging condition in a case in which a radiation image of a subject is acquired by a radiation detector detecting radiation transmitted through the subject in a state in which an object is interposed between the subject and the radiation detector;

deriving a body thickness distribution of the subject based on the radiation image and the imaging condition;

deriving a radiation characteristic of the object based on the body thickness distribution;

deriving a primary ray distribution and a scattered ray distribution of the radiation detected by the radiation detector by using the imaging condition, the body thickness distribution, and the radiation characteristic of the object; and deriving an error between a sum of the primary ray distribution and the scattered ray distribution and a pixel value at each position of the radiation image, updating the body thickness distribution such that the error is smaller than a predetermined threshold value, and repeating derivation of the radiation characteristic based on the updated body thickness distribution and derivation of the primary ray distribution and the scattered ray distribution.

10. A non-transitory computer-readable storage medium that stores a radiation image processing program causing a computer to execute a processing procedure comprising:

a procedure of acquiring an imaging condition in a case in which a radiation image of a subject is acquired by a radiation detector detecting radiation transmitted through the subject in a state in which an object is interposed between the subject and the radiation detector;

a procedure of deriving a body thickness distribution of the subject based on the radiation image and the imaging condition;

a procedure of deriving a radiation characteristic of the object based on the body thickness distribution;

a procedure of deriving a primary ray distribution and a scattered ray distribution of the radiation detected by the radiation detector by using the imaging condition, the body thickness distribution, and the radiation characteristic of the object; and a procedure of deriving an error between a sum of the primary ray distribution and the scattered ray distribution and a pixel value at each position of the radiation image, updating the body thickness distribution such that the error is smaller than a predetermined threshold value, and repeating derivation of the radiation characteristic based on the updated body thickness distribution and derivation of the primary ray distribution and the scattered ray distribution.

* * * * *